US012678090B2

(12) United States Patent
Beard et al.

(10) Patent No.: US 12,678,090 B2
(45) Date of Patent: Jul. 14, 2026

(54) QUANTIFICATION OF INTERMITTENT FUNCTION OF BAROREFLEX FROM CONTINUOUS ARTERIAL PRESSURE DATA

(71) Applicant: THE REGENTS OF THE UNIVERSITY OF MICHIGAN, Ann Arbor, MI (US)

(72) Inventors: Daniel A. Beard, Ann Arbor, MI (US); Daniel E. Michele, Ann Arbor, MI (US); Brian E. Carlson, Ann Arbor, MI (US); Feng Gu, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 950 days.

(21) Appl. No.: 17/353,616

(22) Filed: Jun. 21, 2021

(65) Prior Publication Data

US 2021/0393188 A1 Dec. 23, 2021

Related U.S. Application Data

(60) Provisional application No. 63/041,419, filed on Jun. 19, 2020.

(51) Int. Cl.
*A61B 5/00* (2006.01)
*A61B 5/021* (2006.01)
(Continued)

(52) U.S. Cl.
CPC .......... *A61B 5/4035* (2013.01); *A61B 5/0215* (2013.01); *A61B 5/022* (2013.01);
(Continued)

(58) Field of Classification Search
CPC ..... A61B 5/4035; A61B 5/0215; A61B 5/022; A61B 5/02416; A61B 5/7275;
(Continued)

(56) References Cited

U.S. PATENT DOCUMENTS

2002/0161305 A1* 10/2002 Oka ................... A61B 5/02255
600/490
2016/0029909 A1* 2/2016 Kato .................... A61B 5/7246
600/480

(Continued)

OTHER PUBLICATIONS

Caretaker4 User Manual VER. 4. Caretaker Medical Corp, Apr. 19, 2018, https://www.biopac.com/wp-content/uploads/NIBP-A-MRI-CareTaker4-Guide.pdf (hereinafter—Caretaker4 User Manual). (Year: 2018).*

(Continued)

*Primary Examiner* — Justin Xu

(57) ABSTRACT

An apparatus for measuring arterial pulse and heart rate of a subject includes a wearable sensor assembly configured to be attached to the subject to measure the blood pressure of the subject. The apparatus further includes a signal processor configured to receive blood pressure data from the wearable sensor assembly and to perform time-series analysis on the blood pressure data. The processor then determines baroreflex functionality of the patient, from the blood pressure data. Further, the processor determines an indication of hypertension in the subject from the baroreflex functionality.

17 Claims, 17 Drawing Sheets

WKYM1 10wks. 5:21AM-5:26AM

WKYM1 10wks. 2:30AM-2:35AM

(51) Int. Cl.

| | |
|---|---|
| *A61B 5/0215* | (2006.01) |
| *A61B 5/022* | (2006.01) |
| *A61B 5/024* | (2006.01) |
| *A61B 5/026* | (2006.01) |

(52) U.S. Cl.
CPC ........ *A61B 5/02416* (2013.01); *A61B 5/7275* (2013.01); *A61B 2562/0247* (2013.01)

(58) Field of Classification Search
CPC .......... A61B 2562/0247; A61B 5/0261; A61B 5/02438; A61B 5/7264; A61B 5/021
See application file for complete search history.

(56) References Cited

U.S. PATENT DOCUMENTS

| | | | | |
|---|---|---|---|---|
| 2018/0110464 A1* | 4/2018 | Annoni | .................. | A61B 5/021 |
| 2020/0061316 A1* | 2/2020 | Inoue | ................. | A61M 16/024 |
| 2020/0121258 A1* | 4/2020 | Zhu | .................... | A61B 5/02125 |
| 2021/0296008 A1* | 9/2021 | Novak, Jr. | .............. | G06F 9/451 |

OTHER PUBLICATIONS

Wagenseil et al.; Vascular extracellular matrix and arterial mechanics. Physiol Rev. 2009;89(3):957-89.

Hees, et al.; Effects of normal aging on left ventricular lusitropic, inotropic, and chronotropic responses to dobutamine.—*I Am Coll Cardiol.* 2006;47(7):1440-7.

Nixon et al.; Effect of large variations in preload on left ventricular performance characteristics in normal subjects. *Circulation.* 1982;65(4):698-703.

Joyner et al.; Sex differences and blood pressure regulation in humans. *Exp Physiol.* 2016;101(3):349-55.

Te Riet et al.; Hypertension: renin-angiotensin-aldosterone system alterations. *Circ Res.* 2015;116(6):960-75.

Guyenet PG.; The sympathetic control of blood pressure. *Nat Rev Neurosci.* 2006;7(5):335-46.

Cowley AW, Jr.; Long-term control of arterial blood pressure. *Physiol Rev.* 1992;72(1):231-300.

Carretero et al.; Essential hypertension. Part I: definition and etiology. *Circulation.* 2000;101(3):329-35.

Laurent et al.; The structural factor of hypertension: large and small artery alterations. *Circ Res.* 2015;116(6):1007-21.

Malpas SC.; Sympathetic nervous system overactivity and its role in the development of cardiovascular disease. *Physiol Rev.* 2010;90(2):513-57.

Barrett et al.; What sets the long-term level of renal sympathetic nerve activity—A role for angiotensin II and baroreflexes? *Circulation Research.* 2003;92(12):1330-6.

Guyton AC.; Blood pressure control—special role of the kidneys and body fluids. *Science.* 1991;252(5014):1813-6.

Harrison DG.; The mosaic theory revisited: common molecular mechanisms coordinating diverse organ and cellular events in hypertension. *J Am Soc Hypertens.* 2013;7(1):68-74.

Page IH.; Pathogenesis of arterial hypertension. *J Am Med Assoc.* 1949;140(5):451-8.

Pettersen et al.; Arterial stiffening provides sufficient explanation for primary hypertension. *PLoS Comput Biol.* 2014;10(5):e1003634.

Van Gorp et al.; In spontaneously hypertensive rats alterations in aortic wall properties precede development of hypertension. *Am J Physiol Heart Circ Physiol.* 2000;278: H1241-H7.

Beard et al.; A computational analysis of the long-term regulation of arterial pressure. *F1000Res.* 2013;2:208.

Lerman et al.; Animal Models of Hypertension: A Scientific Statement From the American Heart Association. *Hypertension.* 2019;73(6):e87-e120.

Park, et al.; Forced exercise enhances functional recovery after focal cerebral ischemia in spontaneously hypertensive rats. *Brain Sci.* 2012;2(4):483-503.

Ito et al.; Hypertension following arterial baroreceptor denervation in the unanesthetized dog. *Circ Res.* 1981;48(4):576-91.

DiBona et al.; Dynamic analysis of renal nerve activity responses to baroreceptor denervation in hypertensive rats. *Hypertension.* 2001;37(4):1153-63.

Mancia et al.; Effect of sinoaortic denervation on frequency-domain estimates of baroreflex sensitivity in conscious cats. *Am J Physiol.* 1999;276(6): H1987-93.

Parmer et al.; Baroreflex sensitivity and heredity in essential hypertension. *Circulation.* 1992;85(2):497-503.

Mancia et al.; The autonomic nervous system and hypertension. *Circ Res.* 2014;114(11):1804-14.

Grassi et al.; Baroreflex control of sympathetic nerve activity in essential and secondary hypertension. *Hypertension.* 1998;31(1):68-72.

Monahan et al.; Central arterial compliance is associated with age- and habitual exercise-related differences in cardiovagal baroreflex sensitivity. *Circulation.* 2001;104(14):1627-32.

Gordon et al.; Abnormal Baroreflex Control of Heart-Rate in Prehypertensive and Hypertensive Dahl Genetically Salt-Sensitive Rats. *Hypertension.* 1981;3(3):135-41.

Osborn JW.; Pathogenesis of hypertension in the sinoaortic-denervated spontaneously hypertensive rat. *Hypertension.* 1991;18(4):475-82.

Takeshita et al.; Reduced baroreceptor sensitivity in borderline hypertension. *Circulation.* 1975;51(4):738-42.

Lohmeier et al.; The Baroreflex as a Long-Term Controller of Arterial Pressure. *Physiology.* 2015;30(2):148-58.

Spiering et al.; Endovascular baroreflex amplification for resistant hypertension: a safety and proof-of-principle clinical study. *Lancet.* 2017;390(10113):2655-61.

Lohmeier et al.; Device-Based Neuromodulation for Resistant Hypertension Therapy. *Circ Res.* 2019;124(7):1071-93.

Lohmeier et al.; Prolonged activation of the baroreflex produces sustained hypotension. *Hypertension.* 2004;43(2):306-11.

Lohmeier et al.; Sustained activation of the central baroreceptor pathway in angiotensin hypertension. *Hypertension.* 2002;39(2 Pt 2):550-6.

Burgoyne et al.; Systemic vascular effects of acute electrical baroreflex stimulation. *Am J Physiol Heart Circ Physiol.* 2014;307(2):H236-41.

Heusser et al.; Carotid baroreceptor stimulation, sympathetic activity, baroreflex function, and blood pressure in hypertensive patients. *Hypertension.* 2010;55(3):619-26.

Zeng et al.; PIEZOs mediate neuronal sensing of blood pressure and the baroreceptor reflex. *Science.* 2018;362(6413):464-7.

Kosinski et al.; Computational model-based assessment of baroreflex function from response to Valsalva maneuver. *J Appl Physiol* (1985). 2018;125(6):1944-67.

* cited by examiner

800

804     802

Controller

806       812

Program Memory
820

_830_

_832_

808

Processor

810

RAM

I/O

822

Database   814

826

Display

828

Input Device

824

816

Wearable Sensor

Signal Processing Device

820

WKYM1 10wks. 5:21AM-5:26AM      WKYM1 10wks. 2:30AM-2:35AM

WKYM1 10wks. 5:21AM-5:26AM      WKYM1 10wks. 2:30AM-2:35AM

WKYM1 10wks. 5:21AM-5:26AM      WKYM1 10wks. 2:30AM-2:35AM

|  | WKY | | | | SHR | | | |
|---|---|---|---|---|---|---|---|---|
| n | 12 | 12 | 12 | 12 | 12 | 12 | 12 | 6 |
| wks. | 7 | 10 | 15 | 7 | 10 | 15 | 15 | 8 |
| diet | regular | regular | regular | regular | regular | regular | regular | regular |
| SP | 116.78±2.63 | 123.45±4.11 | 133.80±5.06 | 143.7±6.08 | 160.66±11.21 | 170.64±7.44 | 125.51±2.96 | |
| DP | 76.89±2.60 | 82.44±3.35 | 88.95±3.85 | 91.30±4.46 | 103.59±6.22 | 111.32±4.53 | 86.17±2.53 | |
| MAP | 96.03±2.44 | 101.55±3.58 | 109.67±4.39 | 117.73±5.65 | 131.56±8.80 | 140.07±5.86 | 103.31±2.54 | |
| PP | 39.89±1.55 | 41.01±1.83 | 44.85±1.70 | 52.4±2.27 | 57.07±5.19 | 59.33±4.05 | 39.34±1.85 | |
| STDEV of MAP | 6.11±0.51 | 6.31±0.61 | 6.85±0.74 | 5.57±0.57 | 6.60±0.82 | 7.12±0.61 | 5.21±0.42 | |
| HR | 399.54±14.04 | 357.65±14.42 | 353.32±26.63 | 395.35±19.4 | 369.36±15.26 | 336.48±15.02 | 420.13±18.59 | |
| STDEV of HR | 17.40±2.24 | 19.02±3.10 | 22.96±3.28 | 16.17±2.61 | 17.65±4.09 | 17.37±2.93 | 16.09±3.10 | |

FIG. 4

| | SD | | | SS | | SR |
|---|---|---|---|---|---|---|
| | 6 | 5 | 8 | 4 | 4 | 8 |
| | 11 | 15 | 13 | 20 | 20 | 13 |
| | regular | regular | high-fat | high-fat | regular | high-fat |
| | 131.75±0.95 | 133.62±4.43 | 192.53±14.73 | 198.99±22.35 | 164.49±7.13 | 133.11±6.49 |
| | 93.71±2.30 | 96.29±1.89 | 139.77±12.99 | 145.58±17.77 | 120.14±4.73 | 95.39±7.22 |
| | 109.97±1.64 | 112.23±2.83 | 164.50±13.80 | 170.71±20.04 | 140.89±5.91 | 113.01±6.87 |
| | 38.05±2.05 | 37.33±3.34 | 52.76±2.38 | 53.41±4.58 | 44.35±2.47 | 37.52±3.32 |
| | 5.55±0.36 | 5.25±0.50 | 7.01±0.60 | 7.46±1.17 | 5.86±0.80 | 4.95±0.47 |
| | 397.01±18.13 | 365.78±8.22 | 448.62±21.1 | 421.44±19.82 | 412.77±6.92 | 389.50±18.07 |
| | 18.51±1.20 | 17±2.83 | 24.02±5.36 | 18.49±2.30 | 21.19±6.09 | 18.17±2.47 |

QUANTIFICATION OF INTERMITTENT FUNCTION OF BAROREFLEX FROM CONTINUOUS ARTERIAL PRESSURE DATA

CROSS-REFERENCE TO RELATED APPLICATIONS

The present application claims the benefits of U.S. Provisional Application No. 63/041,419, filed Jun. 19, 2020, entitled "Quantification of Intermittent Function of Baroreflex from Continuous Arterial Pressure Data," the disclosure of which is incorporated herein by reference in its entirety.

STATEMENT OF GOVERNMENT SUPPORT

This invention was made with government support under HL139813 awarded by the National Institutes of Health. The government has certain rights in the invention.

FIELD OF THE DISCLOSURE

The present disclosure relates to health related monitors and, more particularly, to techniques for analyzing blood pressure data and classification of hypertension through baroreflex functionality.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Hypertension, or high blood pressure, is a common condition that can cause other health problems such as organ failure if untreated. Hypertension is often undetected in individuals because people may have hypertension for years without exhibiting or noticing any symptoms. Moreover, there exist no reliable accepted means of predicting the future onset of hypertension in individuals. Untreated hypertension may cause damage to blood vessels and the heart. Undetected and untreated hypertension eventually may lead to heart attack and stroke. Hypertension usually develops over years and eventually affects nearly every person over time.

Monitoring blood pressure and detecting hypertension is typically only performed during a physical examination by a healthcare practitioner, and therefore many people with hypertension go undiagnosed. Wearable devices have the potential to provide continuous monitoring of pressure in a nonintrusive manner. Future healthcare applications making use of data from these devices will require means to assess current and future disease status from the data collected. Therefore, an effective technique for analyzing and assess large amounts of continuous blood pressure data could provide caregivers with a variety of valuable clinical decision-making tools.

Current applications for continuous blood pressure (BP) and blood pressure waveform measurement and analysis mainly use invasive approaches and confined to stationary complex clinical settings such as the intensive care unit (ICU). Hence, the techniques are not suitable for a wide range of applications, including personal healthcare monitoring at home.

At present, assessment of hypertensive disease relies on blood pressure measurements to determine and classify disease status. Although continuous data on blood pressure and heart rate fluctuations contain data on dynamic interactions between the autonomic nervous system and the cardiovascular system, analysis of such data is not effectively done in clinical applications. With the development of low-cost wearable monitoring systems, large quantities of dynamic pressure and heart rate data are becoming available. Therefore, a reliable and effective approach for extracting actionable diagnoses or monitoring effectiveness of interventions from these data is needed.

Non-continuous monitoring systems have been proposed, but these too are problematic. Some of these non-continuous monitoring systems are relatively portable and non-invasive. However, these conventional techniques typically provide limited data from limitations in sensor sensitivity or limitations in data analysis. Moreover, the majority of current noninvasive systems are cumbersome, since inflation of their mechanical cuff (or balloon) obstructs the normal everyday activities of life for the users. Typical blood pressure measurement systems are not continuously wearable; and the information they provide lacks the frequency and granularity required for meaningful signal processing and further, for use in artificial intelligence analysis and machine learning.

In light of these limitations and needs, and given the increased need for new health care delivery models, there is a need for methods that can provide diagnostic insight from continuous noninvasively obtained data to detect, predict, classify, and manage hypertensive disease.

SUMMARY OF THE INVENTION

The present techniques include techniques for identifying pathologies of the autonomic nervous system, diagnosing hypertension associated with autonomic dysfunction, predicting onset and/or progression of hypertensive disease, and predicting optimal treatments for patients with hypertension and other diseases of blood pressure control.

The techniques employ a computational analysis of time-series data on arterial blood pressure and heart rate to identify periods of time during which fluctuations in pressure and heart rate are coupled in a way that that indicates normal operation of the physiological baroreflex. Time periods where the baroreflex is controlling heart rate are labeled "on" states, and time periods where the baroreflex is not controlling heart rate are labeled "off" states. As used herein, "heart rate" and "pulse rate" are interchangeable as the rate of a subject's pulse is the subject's heart rate.

In an embodiment, an apparatus for characterizing the cardiovascular state in individuals includes a wearable sensor assembly configured to be attached to a subject or individual to measure blood pressure of the subject. In some embodiments the wearable sensor assembly may include a plurality of sensors configured to measure heart rate, blood pressure, blood-oxygen level, and other metrics of cardiovascular function. The apparatus further includes a processor configured to receive blood pressure data from the wearable sensor assembly, and perform time-series analysis on the received blood pressure data. The processor determines baroreflex functionality of the subject from the blood pressure data, and determines an indicator of cardiovascular disease state in the subject from the baroreflex activity.

In some examples, the processor is configured to compare the measured blood pressure data with a mathematical regression, or mathematical model of a baroreflex arc. In examples, the measure blood pressure data includes mean arterial pressure data, or the processor may be configured to process the received blood pressure data to determine a mean arterial pressure waveform.

In some examples, the processor determines the indicator of autonomic (or "neurogenic") hypertension and may distinguish between different diagnoses in the subject based on the existence of a correlation relationship between fraction of time in the "off" baroreflex state and mean arterial pressure. In some examples, the processor determines the indicator of autonomic (or "neurogenic") hypertension and may distinguish between different diagnoses in the subject based on differences in trends in mean arterial pressure during baroreflex "on" and "off" states.

In some examples, the processor determines the likelihood of development of hypertension in the subject based on the existence of a correlation relationship between fraction of time in the "off" baroreflex state and mean arterial pressure. The processor may determine an indicator of hypertension with the indicator being one of a likelihood of developing hypertension, a prediction of an onset of hypertension, an identification of etiology of hypertension, a prediction to a responsiveness of a treatment, or an identification of a dysfunction associated with autonomic regulation of heart rate.

In some examples, the processor may determine different physiological mechanisms indicative of a classification of hypertension which may provide insight into which types of therapies a patient may, or may not, respond to.

In some examples, the processor may perform statistical analysis of heart rate and blood pressure data to identify characteristics for diagnoses of dysfunctions of the autonomic nervous system such as the diagnosis and prediction of diabetes, severe preeclampsia, acute stroke, heart failure, chronic kidney disease, atherosclerosis, Parkinson's disease, depression, familial dysautonomia, chronic fatigue syndrome (CFS), and the postural orthostatic tachycardia syndrome (POTS).

In some examples, the processor determines the likelihood of development of hypertension in the subject based on differences in trends in mean arterial pressure during baroreflex "on" and "off" states.

In some examples, the processor, signal processor, or a plurality of processors and controller may be external to the wearable sensor assembly and communicatively connected to the wearable sensor assembly. The processors, and/or processors may each be in communication with the wearable sensor assembly through a wired or wireless connection. Additionally, the processor and/or processors may be configured to receive signals and data from the wearable sensor assembly, provide control signals, data, or information to the wearable sensor assembly (e.g., for calibration of sensors, firmware or sensor update information, etc.), or the processor and/or processors may be in two-way communication with the wearable sensor assembly.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 4 is a table of numerical biometrics pertaining to various rat types for determining hypertensive tendencies.

DETAILED DESCRIPTION

Figure 1:
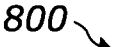
FIG. 1 is a schematic diagram illustrating the various components for implementation of an autonomic baroreflex monitoring system.

The present techniques provide devices and methods for measuring and monitoring blood flow dependent measurements over a sensing region of a subject, such as over a finger, wrist, or other peripheral arterial region. Example devices include wearable sensor devices having two or more sensors of different types.

Physiological control of arterial blood pressure (BP) is achieved via the interaction of multiple organs and organ systems. The pressure waveforms in the systemic arteries are governed by the interactions between ventricular pumping and arterial mechanics, the ionotropic and chronotropic state of the heart, and the preloads driving filling of the left and right sides of the heart. These governing processes are, in turn, regulated by the autonomic nervous system and endocrine signals, notably the baroreflex and the renin-angiotensin-aldosterone system. Since each one of these systems—mechanical, autonomic, and endocrine—has a direct influence on the functions of the others, no single controller of arterial pressure nor single root cause of primary hypertension has been identified. Rather, just as the physiological control of blood pressure is a multifactorial systems-level phenomenon, it may be that the pathophysiology of hypertension is most generally understood as a multifactorial phenomenon. Moreover, because chronic increases in pressure can, in principle, both cause and be caused by mechanical remodeling and changes to autonomic and renal function, it is possible that many different primary insults affecting different systems could all drive the system toward the same multifactorial pathological phenotype.

The arterial baroreflex controls heart rate via a negative feedback system, where increases in arterial pressure cause decreases in heart rate and decreases in pressure cause increases in heart rate. Dysfunction of the autonomic systems associated with the baroreflex are associate with numerous diseases and disorders. Disclosed herein are methods for analyzing time-course arterial pressure data to identify and characterize a markedly intermittent functioning of the baroreflex arc. Applying this methodology to data from rats features of the intermittent nature of the baroreflex are identified which are useful in predicting hypertensive disease and in distinguishing different etiologies of disease in different rat models of hypertension. Also, the methods may be successfully applied to analyze arterial pressure time-series data obtained from human subjects, and the features identified in the data from animal models can be identified in the human data. Further, a wearable monitor for measuring physiological data may be used to perform the measurements of the arterial pressure and heart rate.

The disclosed system and method have the potential to be adopted for numerous health care applications. For example, when a patient is diagnosed with hypertension, physicians typically start treatment by prescribing medicine to determine how the patient reacts to the medicine and specifically if the medicine is effective in treating a patients form of hypertension. A patient may be prescribed a diuretic, an angiotensin-converting enzyme (ACE) inhibitor, an angiotensin II receptor blocker (ARB), a calcium channel blocker, an alpha blocker, an alpha-beta blocker, a beta blocker, an aldosterone antagonist, a renin inhibitor, a vasodilator, a central-acting agent, or another medication for medicating hypertension. Each medication, or combination of medications, prescribed are target different physiological mechanisms and the medication efficacy depends on the type of hypertension and specific cause of hypertension. Therefore, a number of trials of different medications is typically required before a proper diagnosis and prescription is found for a given hypertensive patient. It is therefore beneficial to know a classification of the hypertension to give insight into which medication is likely to be effective for a given hypertensive patient. The system and methods disclosed may allow for the classification of specific mechanisms of hypertension, and/or the ability to rule out specific types of classifications of hypertension which reduces the number of medication trials for a patient, and the amount of time and money spent for a proper diagnosis and treatment to be found. Further, the disclosed system and methods use non-perturbative techniques to determine indicators of hypertension.

FIG. 1 is an example schematic block diagram 800 illustrating the various components used in implementing an example embodiment of an autonomic baroreflex monitoring system discussed herein. A signal-processing device 802 (or "signal processor") may be coupled to a patient 820 via one or more wearable sensors 816 (or a "wearable sensor assembly") in accordance with executing the functions of the disclosed embodiments. The wearable sensor assembly having wearable sensors 802 may include a wrist band, an armband, a waist band, an ankle band, a head band, a patch that adheres to a patient, a watch, other jewelry with sensors, a garment, or another item that may be operatively coupled to a patient with sensors for measuring biometrics of the patient. The one or more wearable sensors 816 may be coupled to the patient via an elastic band, a Velcro band, an adhesive, a belt, or via a garment such as wearing a shirt or pants, among other means. Further, the wearable sensor assembly may be in physical contact with the patient, or the wearable sensor array may not be in direct physical contact with the patient, for example, by using optical sensors in a set of glasses.

The signal-processing device 802 may have a controller 804 operatively connected to the database 814 via a link 822 connected to an input/output (I/O) circuit 812. It should be noted that, while not shown, additional databases may be linked to the controller 804 in a known manner. The controller 804 includes a program memory 806, one or more processors 808 (may be called microcontrollers or a microprocessors), a random-access memory (RAM) 810, and the input/output (I/O) circuit 812, all of which are interconnected via an address/data bus 820. It should be appreciated that although only one processor 808 is shown, the controller 804 may include multiple microprocessors 808. Similarly, the memory of the controller 804 may include multiple RAMs 810 and multiple program memories 806. Although the I/O circuit 812 is shown as a single block, it should be appreciated that the I/O circuit 812 may include a number of different types of I/O circuits. The RAM(s) 810 and the program memories 806 may be implemented as semiconductor memories, magnetically readable memories, and/or optically readable memories, for example. A link 824, which may include one or more wired and/or wireless (Bluetooth, WLAN, etc.) connections, may operatively connect the controller 804 to a wearable sensor 816 through the I/O circuit 812. The wearable sensor 816 may be operatively connected to the patient 820. The wearable sensor 816 may include an optical heart rate sensor, a physical pressure sensor, an electrocardiography sensor, a photoplethysmography sensor, a sphygmomanometer, an inflatable cuff, a digital blood pressure monitor, or another sensor capable of measuring arterial pressure and/or pulse pressure.

The program memory 806 and/or the RAM 810 may store various applications (i.e., machine readable instructions) for execution by the processor 808. For example, an operating system 830 may generally control the operation of the signal-processing device 802 and provide a user interface to the signal-processing device 802 to implement the process 100 described herein. The program memory 806 and/or the RAM 810 may also store a variety of subroutines 832 for accessing specific functions of the signal-processing device 802. By way of example, and without limitation, the subroutines 832 may include, among other things: a subroutine for taking measurements with the wearable sensor 816, a subroutine for filtering measurement (or data) from the wearable sensor 816, a subroutine for performing signal decomposition on raw signal data from the wearable sensor 816, and a subroutine for extracting one or more features of a sensing region from the raw signal data from the wearable sensor 816. The subroutines 832 may also include other subroutines, for example, implementing software keyboard functionality, interfacing with other hardware in the signal-processing device 802, etc. The program memory 806 and/or the RAM 810 may further store data related to the configuration and/or operation of the signal-processing device 802, and/or related to the operation of the one or more subroutines 832. For example, the data may be data gathered by the wearable sensor 816, data determined and/or calculated by the processor 808, etc. In addition to the controller 804, the signal-processing device 802 may include other hardware resources. The signal-processing device 802 may also include various types of input/output hardware such as a visual display 826 and input device(s) 828 (e.g., keypad, keyboard, etc.). In an embodiment, the display 826 is touch-sensitive, and may cooperate with a software keyboard routine as one of the software routines 832 to accept user input. It may be advantageous for the signal-processing device 802 to communicate with a broader medical treatment network (not shown) through any of a number of known networking devices and techniques (e.g., through a commuter network such as an hospital or clinic intranet, the Internet, etc.). For example, the testing apparatus may be connected to a medical records database, hospital management processing system, health care professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

Although depicted as separate entities or components in FIG. 1, it is understood that any or the entire signal processing functionality and/or components of the signal-processing device 802 may be combined with a wearable sensor assembly, such as the wearable sensor 816. In this manner, a wearable sensor may both gather data about the patient 820 and process the gathered data to extract one or more waveform features, as discussed further below.

Also, although depicted as a single component in FIG. 1, the wearable sensor 816 may include multiple of the same type or different types of sensors. For example, the wearable sensor 816 may include both a piezoelectric pressure sensor for measuring raw signal pressure data and a secondary sensor for collecting photoplethysmograph derived blood flow and hemoglobin oxygen saturation data. Generally, the wearable sensor 816 may include one or more piezoelectric sensors or electrodes. In some examples, the wearable sensor 816 may be implemented with one or more of a variety of other (or secondary) sensors, such as temperature sensors, motion sensors, actigraphy sensors, galvanic skin response sensors, impedance sensors, etc.

In some examples in which the wearable sensor 816 includes a secondary sensor for collecting photoplethysmograph derived blood flow data, the secondary sensor may provide (e.g., to a signal processing computer) a waveform that is flow related. The changes in the waveform may provide information related to the arterial tone at both the site of measure and, in some cases, more centrally (i.e., at a central artery such as the aorta and carotid arteries). When compared with central aortic pressure, peripheral arterial waveforms have higher systolic pressure, lower diastolic pressure, and greater pulse pressure, but despite differences between peripheral and central arterial waveforms, the mean arterial pressure (MAP) in the aorta is just slightly greater than MAP in the radial artery.

Changes in the waveform from the secondary sensor along with changes in a waveform from the piezoelectric sensor (amplitude, width, time differences in peaks, delta responses to provocative movements such as breathing, volume infusion, etc.) may provide complementary information about the patient as it relates to circulating vascular volumes and vascular tone. Thus, the ability to look at these two signals together allows for determining which components are responsible for changes and as well as how best to favorably affect changes, such as providing medications to tighten or relax arterial wall tone.

EXAMPLES

A radio-telemetry system (PA-C10, Data Sciences International; St. Paul, MN) was used to collect real-time arterial pressure waveforms data. Seven days after implantation of the telemetry system, the arterial pressure was recorded for 5 minutes continuously (500. Hz) for the whole dark-cycle (6 pm-6 am). Data from spontaneously hypertensive rats (SHR) and Wistar-Kyoto (WKY) were recorded at 7 weeks, 10 weeks, and 15 weeks of age. Data from Sprague-Dawley (SD) animals were recorded at 8 weeks, 11 weeks, and 15 weeks. Data from salt-sensitive (SS) rats fed on high- and control fat diets were collected at 13 weeks and 20 weeks. Data from salt-sensitive (SR) rats fed on high fat diets were collected at 13 weeks. Vessel ultrasound was also performed to measure the elasticity of the aorta and carotid arteries at the same times.

Time-series analysis of the telemetry data is based on the assumption that when the baroreflex is operational, changes in arterial pressure should affect changes in heart rate: transient increases in mean and/or pulse pressure should be followed by proportional increases in pulse interval or RR interval, while transient decreases in pressure should be followed by proportional decreases in RR interval. A linear filter-based approach was used to distinguish time windows when the baroreflex is and is not functioning—that is, times when the expected relationship between pressure and heart rate does and does not exist.

Conscious blood pressure was recorded continuously during the active dark cycle (6 pm-6 am). One five-minute window of uncorrupted data from each one-hour block was analyzed for each animal at each age studied. Hence, a total of 12 individual five-minute time courses of pressure representative of each hour were collected of the 12-hour raw data for analysis. The five-minute periods were selected as close as possible to the middle of each hour. Systolic (SP) and diastolic (DP) pressures were taken as the local maxima and minima of the pulse pressure signal, and mean arterial pressure (MAP) was approximated at each cardiac cycle $t_j$ for j=1, N and N the total number of cardiac cycles in each five-minute period as $$MAP(t_j) = (SP(t_j) + 2DP(t_j))/3. \qquad (1)$$

Figure 2A:
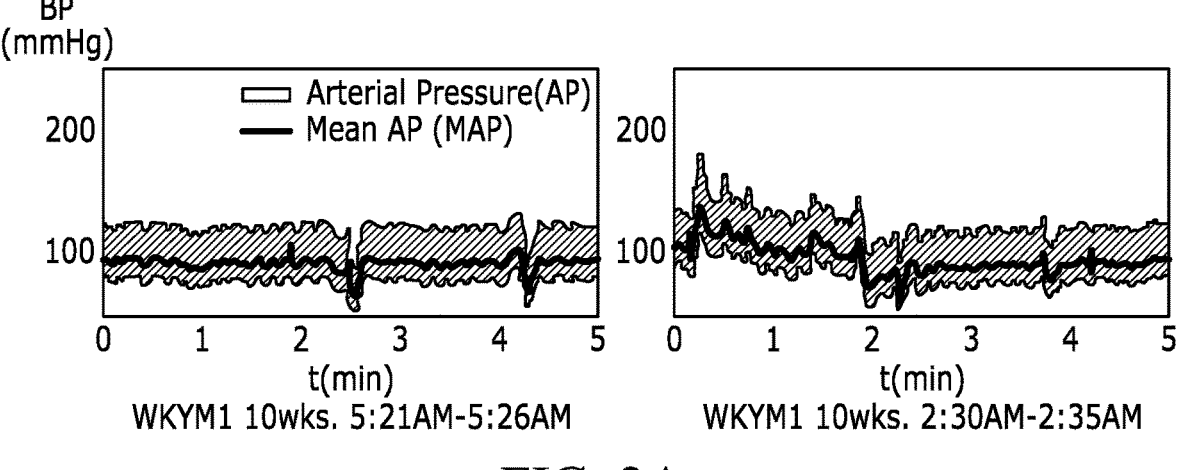
FIG. 2A shows two plots of blood pressure vs time data for two continuous five-minute periods of time obtained from a Wistar-Kyoto (WKY) rat at 10 weeks.

FIG. 2A shows two examples of plots of continuous five-minute time-course blood pressure data obtained from a WKY rat at 10 weeks. Data on R-R interval (RR(t), heart rate=1/RR) are compared to predictions from a linear filter to analyze the autonomic response to the Valsalva maneuver in human subjects. The model assumes that RR(t) determined by the autonomic baroreflex is captured by a first-order linear filter applied to the mean arterial pressure, MAP(t):

$$\tau \frac{dRR}{dt} + RR(t) - R_0 = \alpha MAP(t). \qquad (2)$$

where α, ▯ , and $R_0$ are parameters. An alternative mathematical model may be used and is likely to give equivalent results for the present applications, as long as the alternative model captures the central phenomenon that a change in blood pressure effects a proportional change in RR. Here, the parameter α represents the baroreflex sensitivity (measured in units of change in RR interval time per unit change in pressure). The parameter ▯ ▯ is a time constant that determines how quickly change in BP will generate change in HR. The inverse 1/▯ is the response rate. Assuming a piecewise constant right-hand side of Equation (1) over an individual beat of duration Δt, the solution to Equation (1) is:

$$RR(t_j) = RR(t_{j-1} - \Delta t)e^{-\frac{\Delta t}{\tau}} + \left(1 - e^{-\frac{\Delta t}{\tau}}\right)(\alpha MAP(t_{j-1} - \Delta t) + R_0). \qquad (3)$$

Figure 2B:
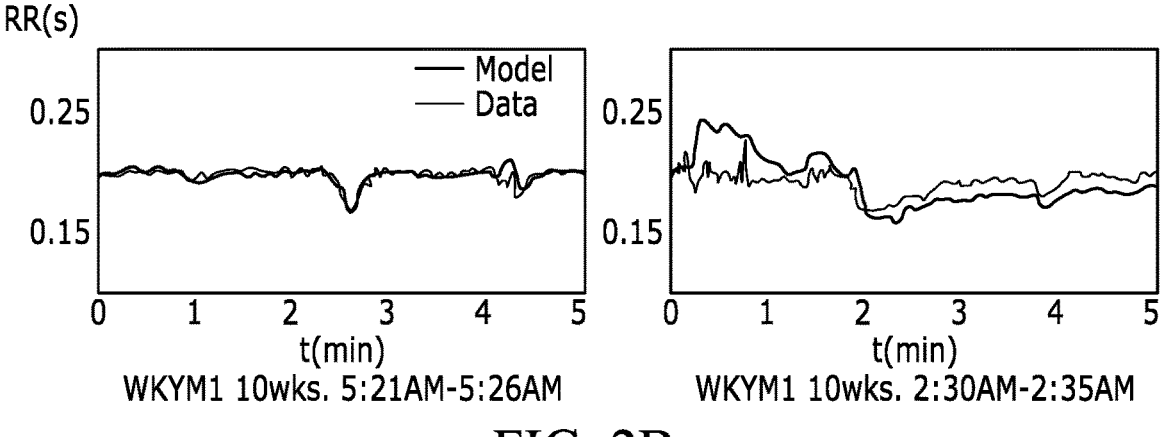
FIG. 2B shows plots of pulse interval (RR) data over time compared to mathematical fits for models of the baroreflex arc.

For the rat data sets, each five-minute time course of BP data is analyzed separately. FIG. 1A shows two examples of continuous five-minute time-course pressure data obtained from a 10-wk WKY rat. Systolic (SP), diastolic (DP), and mean arterial (MAP) pressures and pulse intervals (RR) are extracted for each cardiac cycle in each record. Initial estimates of ▯ and ▯ are obtained by fitting the data to the linear filter model of Equations (1) and (2). The expected relationship between the parameter $R_0$ and the gain ▯ ▯ is used as a constraint:

$$R_0 = \langle RR \rangle - \alpha \langle MAP \rangle. \qquad (3)$$

where ⟨ · ⟩ indicates the average value over a given five-minute time course. This approach yields substantial variability in the ability of the model to match the data, as illustrated in FIG. 2B. This approach yields substantial variability in the ability of the model to match the data as illustrated in FIG. 2B, which shows example plots of the mathematical model fitting the pulse interval data well (left panel) and poorly (right panel).

The RR data are compared to the fits (solid red lines) to a simple mathematical model of the baroreflex arc in FIG. 2B. When the baroreflex is functioning, as in the left panels of FIGS. 2A and 2B, transient reductions in MAP result in transient reductions in RR; transient peaks in MAP are followed by transient peaks in RR. The dynamic coupling between MAP and RR is reflected in a close match between the model and the data in the left panel of FIG. 2B. For the time window illustrated in the right panels of FIGS. 2A and 2B the MAP and RR interval are not coupled in a way that would be predicted by physiological operation of the baroreflex. For example, transient pressure increases are followed by transient increases in heart rate. The lack of physiological coupling of the baroreflex is reflected in the lack of a match between model simulations and data in the right panel of FIG. 2B. An assessment of the relatively bad fits suggests an intermittent engagement and disengagement of the baroreflex-mediated control of heart rate. At times the RR interval tends to be changing in the direction predicted by the model. These time periods are identified as times when the baroreflex arc is operating in an "on" state. Time periods when the model cannot be made to coincide with the data are identified as representing baroreflex "off" states. To identify and quantify time periods where the baroreflex is "on" or "off", the change in RR interval over a fixed period Tis compared to the change in RR interval predicted by the model. For calculations shown here the period for comparison is set to T=10 seconds. Similar results are obtained when T is half or twice this value.

To determine the time constant τ and gain α for each subject a given age, the cost function (J) is minimized, and the relative difference in the variability of the heart rate between the model output and the data is calculated. The variability is quantified by computing the slope of the line of regression within a fixed window T centered at cardiac cycle $t_j$ during a five-minute time course i=1, . . . , 12 for both the model output ($\mu_{m,i,j}$) and the data ($\mu_{d,i,j}$). Thus $\mu_{m,i,j}$ and $\mu_{d,i,j}$ are unitless numbers reflecting the local rates of change in RR per unit time. Simultaneous fits are generated for all 12 five-minute data sets obtained from a given animal at a given age. T was chosen to be 10 seconds, though largely equivalent results are obtained when T is set to half or twice this value. The standard deviation of the slopes of the model output $\sigma_m$=std($\mu_m$) and data $\sigma_d$=std($\mu_d$) were computed for $$\mu_m = [\mu_{m,1,1}, \cdots, \mu_{m,1,N}, \mu_{m,2,1}, \qquad (5)$$
$$\cdots, \mu_{m,2,N}, \cdots, \mu_{m,12,1}, \cdots, \mu_{m,12,N}], \text{ and}$$

$$\mu_d = [\mu_{d,1,1}, \cdots, \mu_{d,1,N}, \mu_{d,2,1},$$
$$\cdots, \mu_{d,2,N}, \cdots, \mu_{d,12,1}, \cdots, \mu_{d,12,N}].$$

Hence, the cost functional was minimized to obtain optimal parameter values for τ and α for each subject at each age.

$$J = \left| \frac{\sigma_m}{\sigma_a} - 1 \right| \qquad (6)$$

Figure 2C:
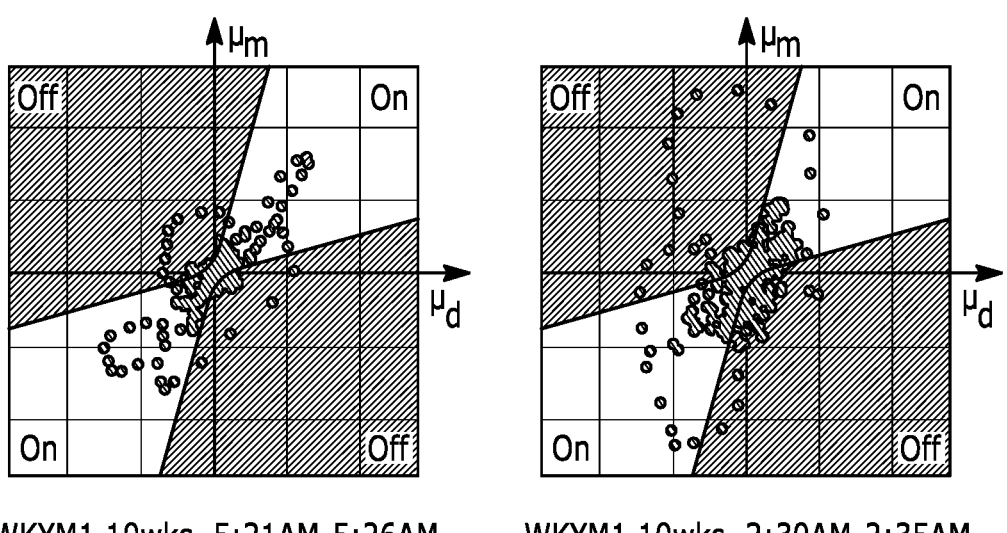
FIG. 2C shows plots of rate of change in RR interval expected from a functioning baroreflex ($\mu_m$) versus the observed rate of change of RR interval ($\mu_d$) for determining "on" and "off" states from the blood pressure time-course data.
Figure 2D:
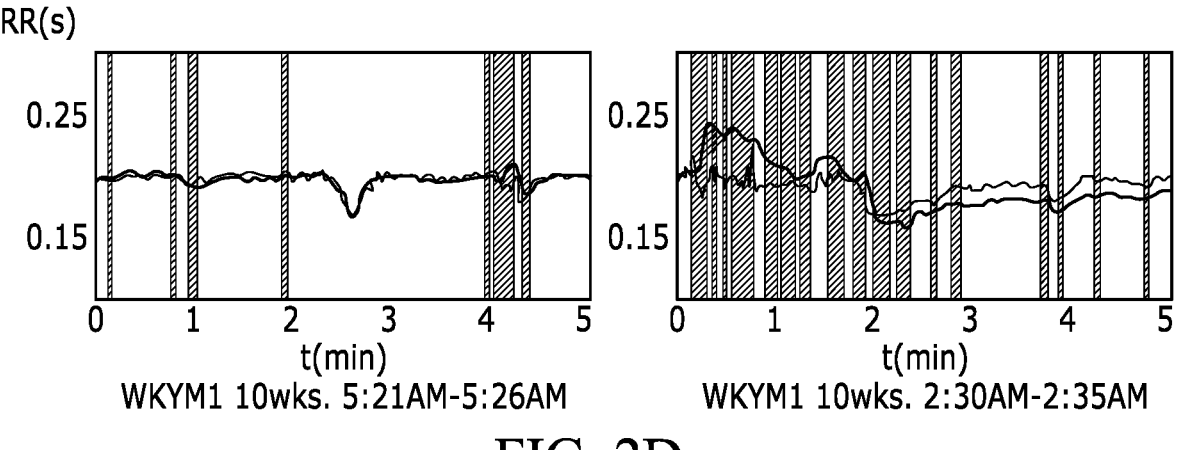
FIG. 2D shows plots of RR over time of the "on" and "off" states for the blood pressure time-course given in FIGS. 2A and 2B.
Figure 2E:
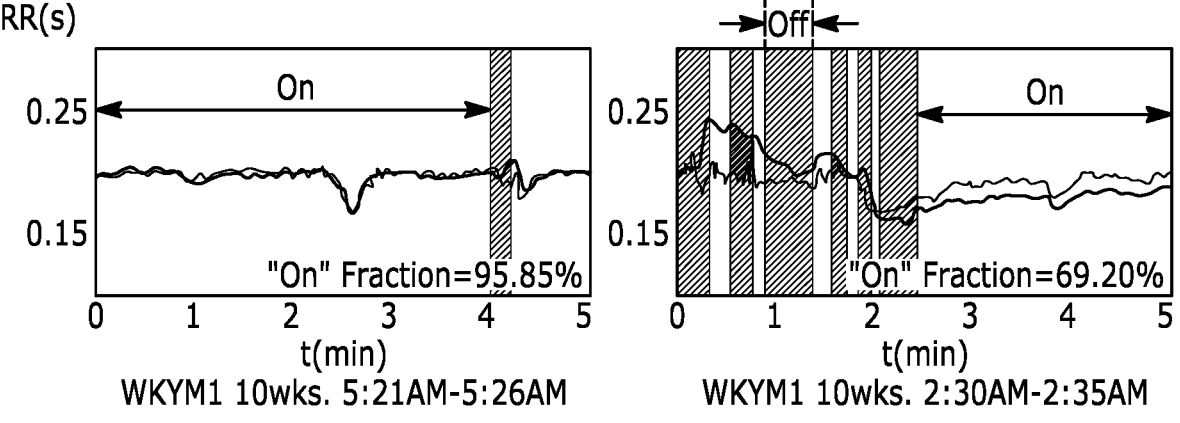
FIG. 2E is a plot of the RR over time data presented in FIG. 2D with noise filtered out, resulting in the final determinate of on and off states for these time windows.

FIG. 2C shows plots of rate of change in RR interval expected from a functioning baroreflex ($\mu_m$) versus the observed rate of change of RR interval ($\mu_d$) for determining "on" and "off" states from the blood pressure time-course data. To compare the model predicted change in RR interval to the observed data and determine "on" and "off" states from the blood pressure time-course data, regions were located in the plot of the slopes $\mu_m$ versus $\mu_d$ in FIG. 2C for which the linear response model does not predict the observed response, that is, when the points lie away from the y=x line. The boundary for the "on" and "off" domains are demarcated by the hyperbola $$\mu_m^2 + \mu_d^2 - a\mu_m\mu_d = r^2 \qquad (7)$$

which is about y=x symmetry. The parameter r is the magnitude of the x- and y-intercepts and $\alpha$ is a parameter determining the curvature of the hyperbola. To exclude relatively small fluctuations in $\mu$ from being identified as representing "off" states, the parameter r is set to $\frac{1}{5}\sigma_d$ representing the 7-week WKY cohort. The unitless parameter $\alpha$ is set to a value of 4. The computed trends are not sensitive to the choice of $\alpha$. In plotting $\mu_m$ versus $\mu_d$. "On" states are determined to be indicated by points that fall inside the hyperbola (white region) bounded by the curves. Specifically, the on states are durations of time where the measured increases in arterial pressure are followed by increases in RR, and measured decreases in arterial pressure are followed by decreases in RR due to the action of the arterial baroreflex. The off states are durations where the relationship between arterial pressure and RR is not present (i.e., there is no discernible relationship between the trends of the arterial pressure and the RR). The points that lie outside the hyperbola (gray regions) are considered "off". FIG. 2D shows plots of RR over time that that display the "on" and "off" states for the blood pressure time-course given in FIGS. 2A and 2B, which white shading representing "on" and gray shading representing "off". FIG. 2E is a plot of the RR over time data presented in FIG. 2D with the noise filtered out, resulting in the final determinate of on and off states for these time windows.

We apply a smoothing procedure to filter out noise in the sequences of "on" and "off" designations. A cardiac cycle $t_j$ is initially assigned a value of 1 if it is "on" and 0 if it is "off". The resulting time series is smoothed by iteratively computing the 10-second moving average of the data until the result converges. After smoothing, time points that are <0.5 are "off" and ≥0.5 are "on". FIG. 1E illustrates the final "off" and "on" states after smoothing the results from FIG. 1D.

"On" fraction. We define the index "on" fraction as $$\text{"On" fraction} = \frac{\text{Total time in "on" state}}{\text{Total time}}, \qquad (8)$$

which describes the fraction of time when an individual animal at a given age is in the "on" state. It may be determined that a hypertensive person or organism, and/or a person or organism that is susceptible to developing hypertension exhibits an "on" fraction below a threshold of 40%. The "on" fraction may decrease with age depending on health conditions of the person or organism. It may also be determined that the intermittent functioning of the baroreflex is one of multiple causes of developing hypertension in an individual or organism.

Figures 3A, 3B, 3C:
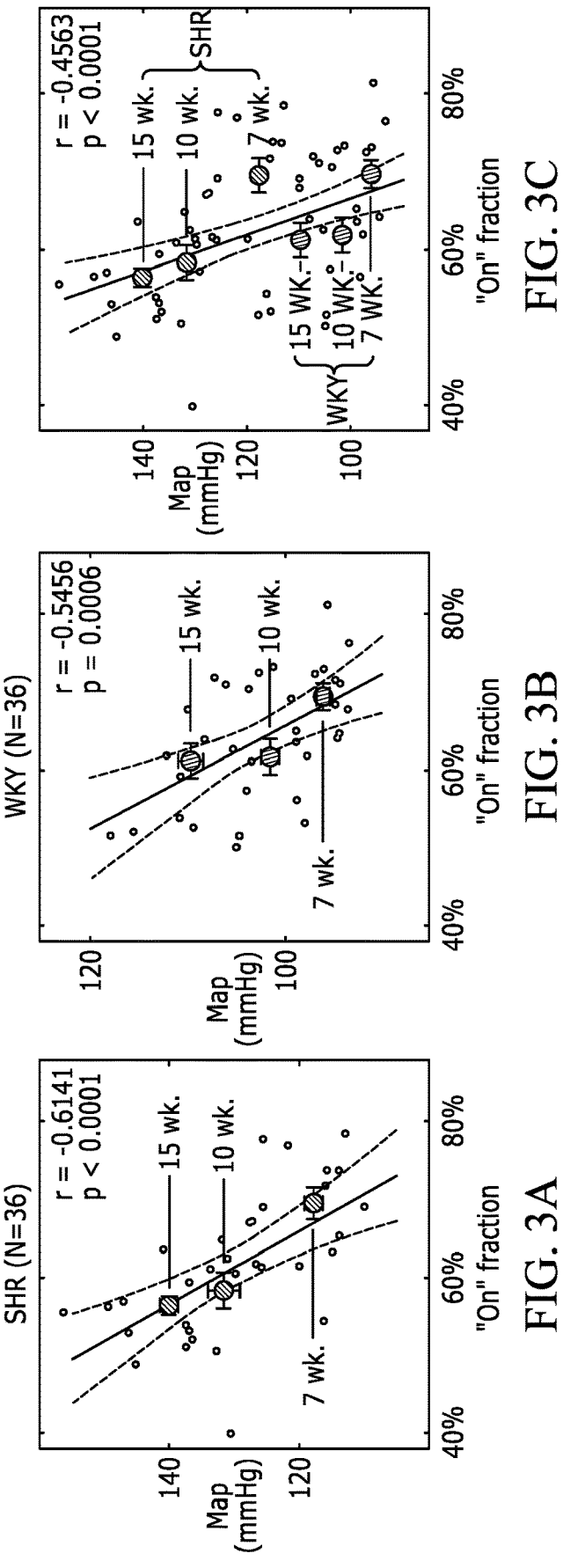
FIG. 3A is a plot of blood pressure versus "on" fraction data for 36 Spontaneously Hypertensive (SHR) rats at 7, 10, and 15 weeks.
FIG. 3B is a plot of blood pressure versus "on" fraction data for 36 WKY rats at 7, 10, and 15 weeks.
FIG. 3C is a plot of the combined blood pressure versus "on" fraction data for 36 SHR rats and 36 WKY rats at 7, 10, and 15 weeks.

FIGS. 3A-3F and FIG. 4 summarize data on the relationships between baroreflex function, hypertension, and age. FIGS. 3A-3F presents multiple plots of blood pressure versus "on" fraction, and FIG. 4 is a table of numerical findings. The estimated baroreflex sensitivity is not found to be different between any of the strains or ages studied as shown by the table in FIG. 4. No correlations were found between baroreflex sensitivity and MAP, arterial mechanics, or age. However, the on fraction was found to decreasing with MAP and age (FIGS. 3A and 3D) in the SHR and WKY. In addition, the average on fraction was lower in the SHR than in the WKY, as shown in FIG. 3C. Combining the data on MAP and on fraction in WKY and SHR rats, it can be determined that the "on" fraction is a strong predictor of MAP and degree of hypertension.

Figures 3D, 3E, 3F:
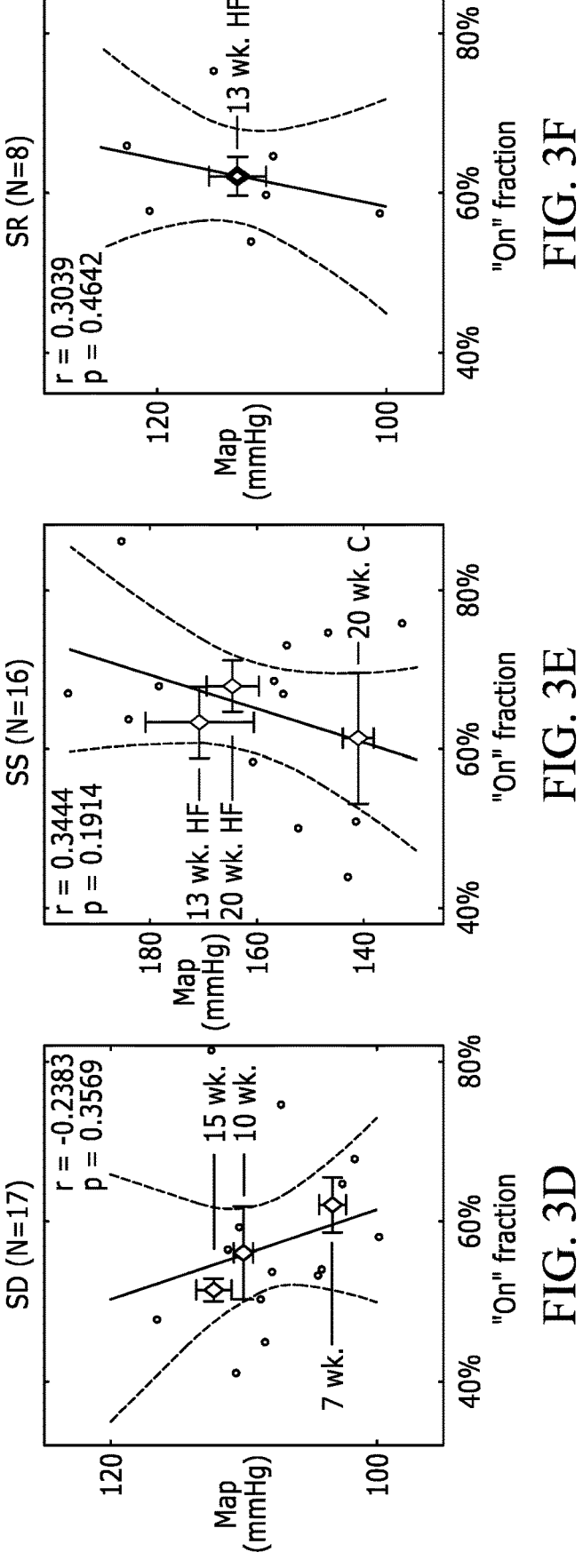
FIG. 3D is a plot of blood pressure versus "on" fraction for 17 normotensive Sprague-Dawley (SD) rats at 7, 10, and 15 weeks.
FIG. 3E is a plot of blood pressure versus "on" fraction for 16 hypertensive Dahl Salt Sensitive (SS) rats with two different diets.
FIG. 3F is a plot of blood pressure versus "on" fraction for 8 normotensive Dahl Salt Resistant (SR) rats at 13 weeks.

Given that the SHR and WKY share similar origins and genetic background, the predictive relationship between on fraction and MAP was investigated to determine if the relationship is a universal phenomenon or unique to the SHR/WKY genetic background. FIGS. 3D and 3F are plots of MAP versus on fraction from analogous analysis performed on the SS, SR, and SD rats. FIG. 3D shows that results from conscious direct BP measurements in SD rats at 8, 11, and 15 weeks of ages show no significant relationship between MAP and on fraction. FIG. 3E shows that data from hypertensive SS rats (induced from high-fat feeding) and from normotensive control-diet SS rats also show no significant relationship between MAP on fraction. Finally, in FIG. 3F, data from normotensive SR rats on high-fat diet also show no such relationship. Thus among the animal models studied here, only the SHR and WKY strains show a predictive relationship between baroreflex on fraction and MAP.

To probe how "on" fraction affects BP regulation in the SHR/WKY model, probability density distributions of MAP observed during baroreflex on and off states were constructed. Each of the probability densities has a mean and variance which may be indicative of hypertension. For example, a wider distribution (i.e., larger variance), or a shift in the probability density (e.g., a larger or smaller mean) may be indicative of hypertension. Further, the indicator of hypertension may be determined by comparing probability densities of the on functionality durations, and the off functionality durations of blood pressure data. Comparing probability density functions may include comparing a mean, variance, skew, and/or a shape or profile of the probability density functions. Further, the indicator of hypertension may be determined by comparing a probability density function of a subject with a probability density function of normal or non-hypertensive baroreflex functionality.

Figure 5A:
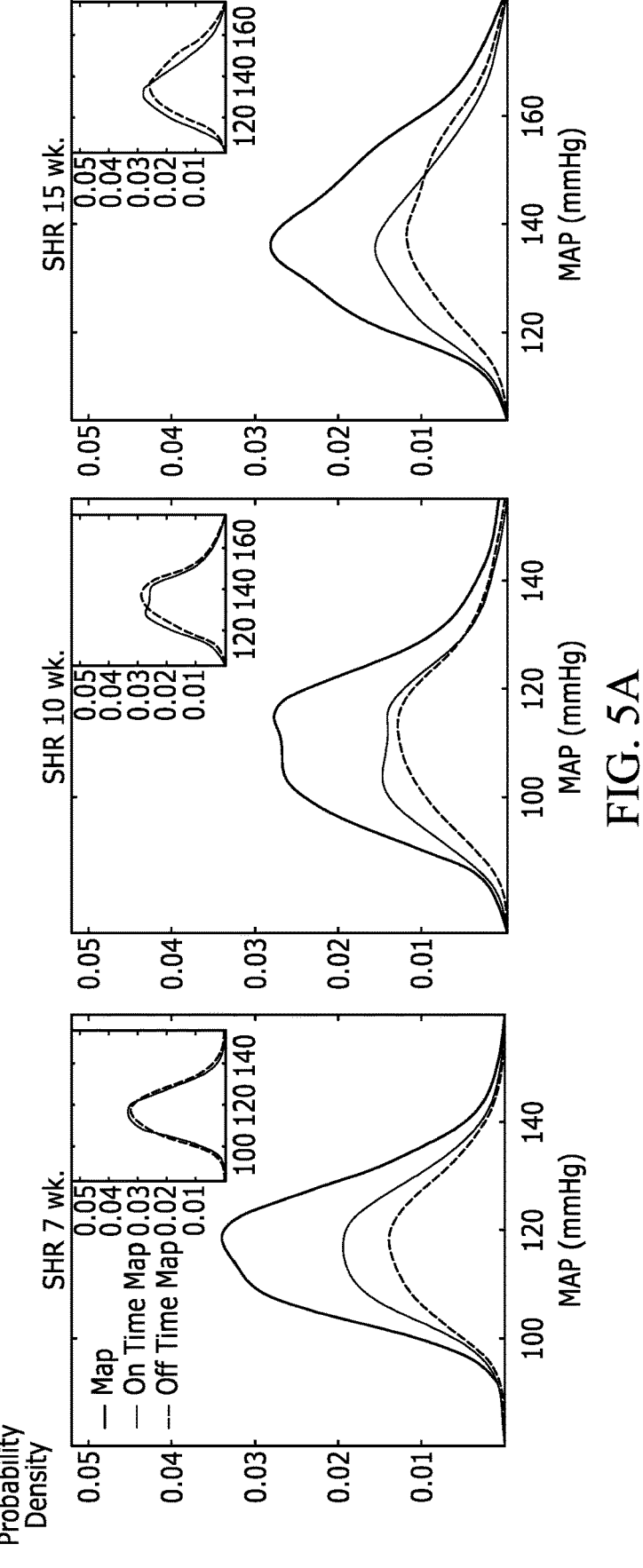
FIG. 5A shows plots of rat probability density vs mean arterial pressure for SHR rats at 7, 10, and 15 weeks.
Figure 5B:
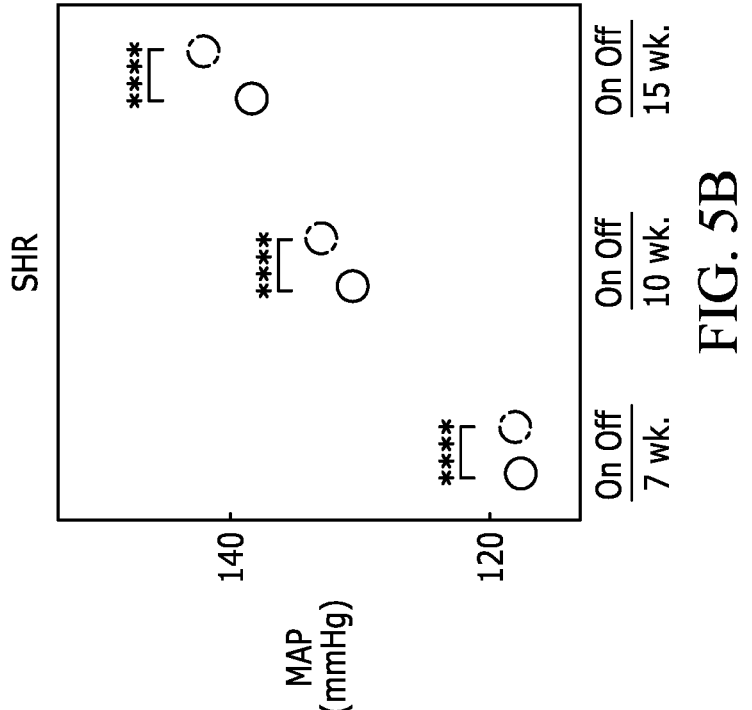
FIG. 5B is a plot of mean arterial pressure over time for 7, 10, and 15 weeks.
Figure 5C:
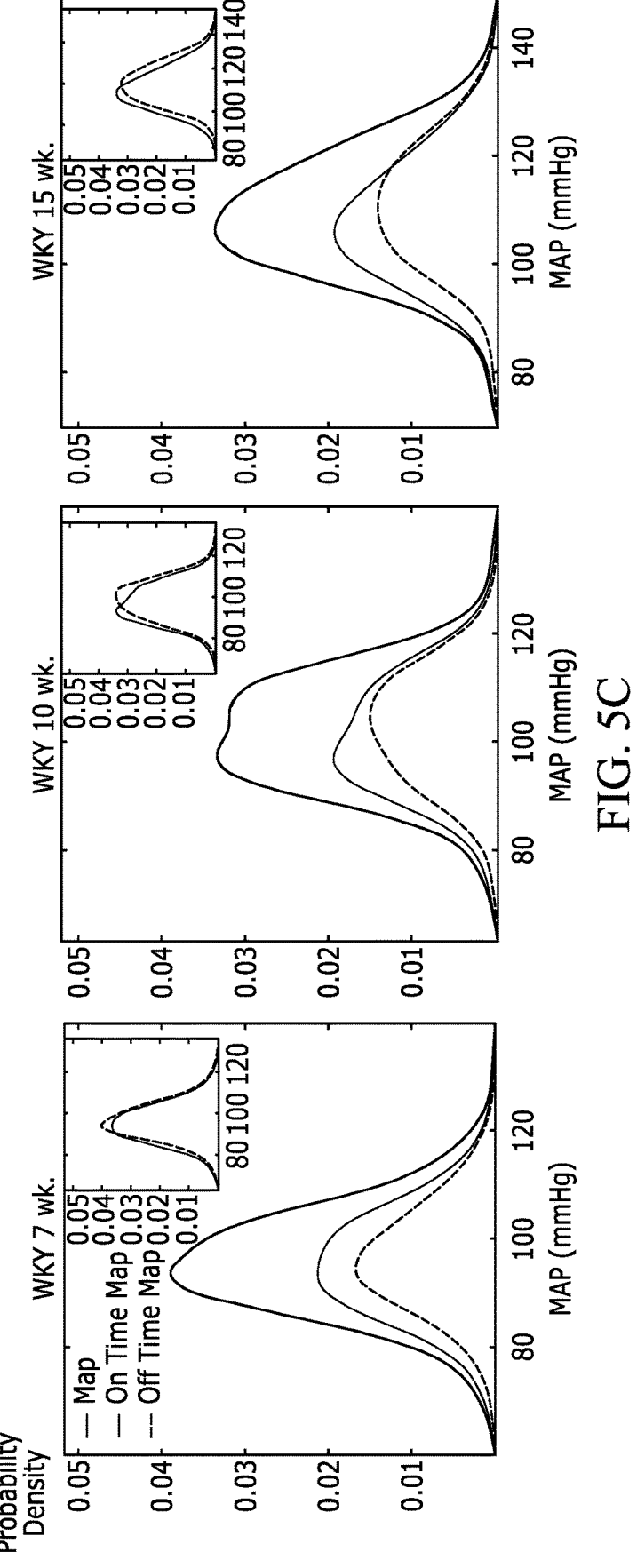
FIG. 5C shows plots of rat probability density vs mean arterial pressure for WKY rats at 7, 10, and 15 weeks.
Figure 5D:
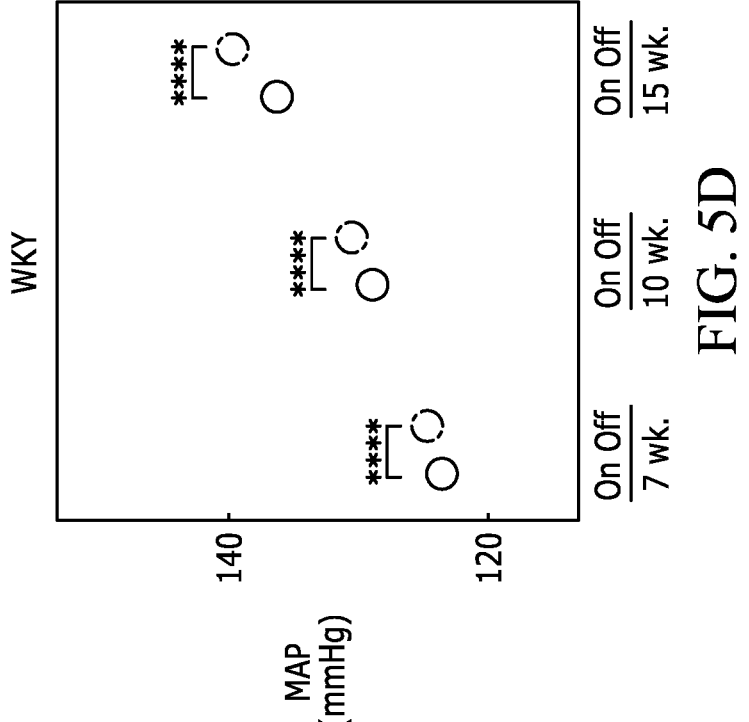
FIG. 5D is a plot of mean arterial pressure over time for 7, 10, and 15 weeks.
Figure 5E:
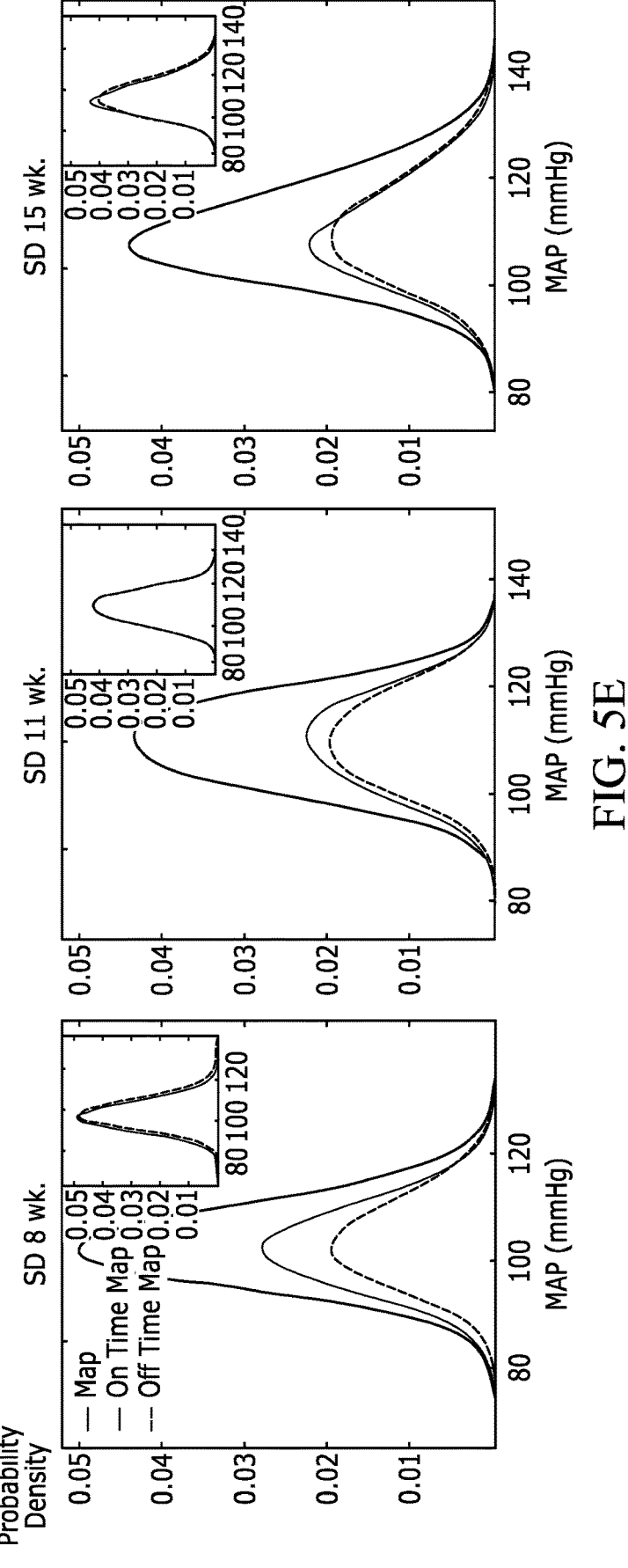
FIG. 5E shows plots of rat probability density vs mean arterial pressure for SD rats at 8, 11, and 15 weeks.
Figure 5F:
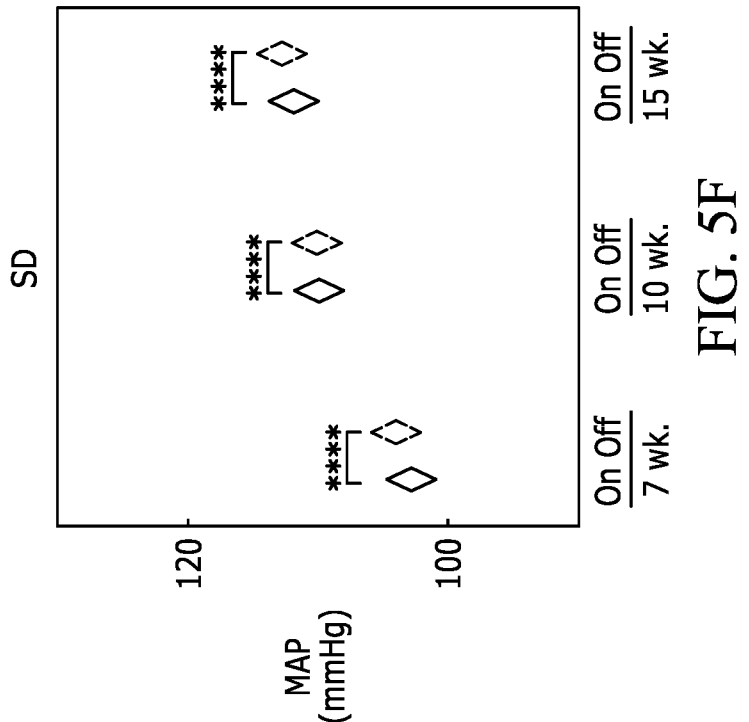
FIG. 5F is a plot of mean arterial pressure over time for 7, 10, and 15 weeks.

FIG. 5A-5F shows plots of the probability densities of MAP measured at the per-beat level during on and off states in SHR, WKY, and SD strains at the three ages studied. In SHR and WKY animals the pressure distributions become wider with increased age, indicating larger fluctuations in pressure compared to younger animals. The widest distribution (most variable MAP) is observed for the 15-week SHR. FIGS. 5B, 5D, and 5F plot the average MAP values obtained during on and off times at different ages and in the different strains. MAP is the per-beat mean arterial pressure and thus fluctuates, as indicated in the figures. The average MAP is denoted <MAP>. In all rat strains and at all ages, the <MAP> is higher during baroreflex off times than it is during on times. However the observed difference in <MAP> between on and off times becomes greater than 1.6 mmHg only for the SHR and WKY groups at ages 10 and 15 weeks. In SD rats the difference in <MAP> is always less than 0.9 mmHg. FIGS. 5A and 5C show that similarly small differences are observed for the SS and SR animals studied.

Figures 6A, 6B, 6C:
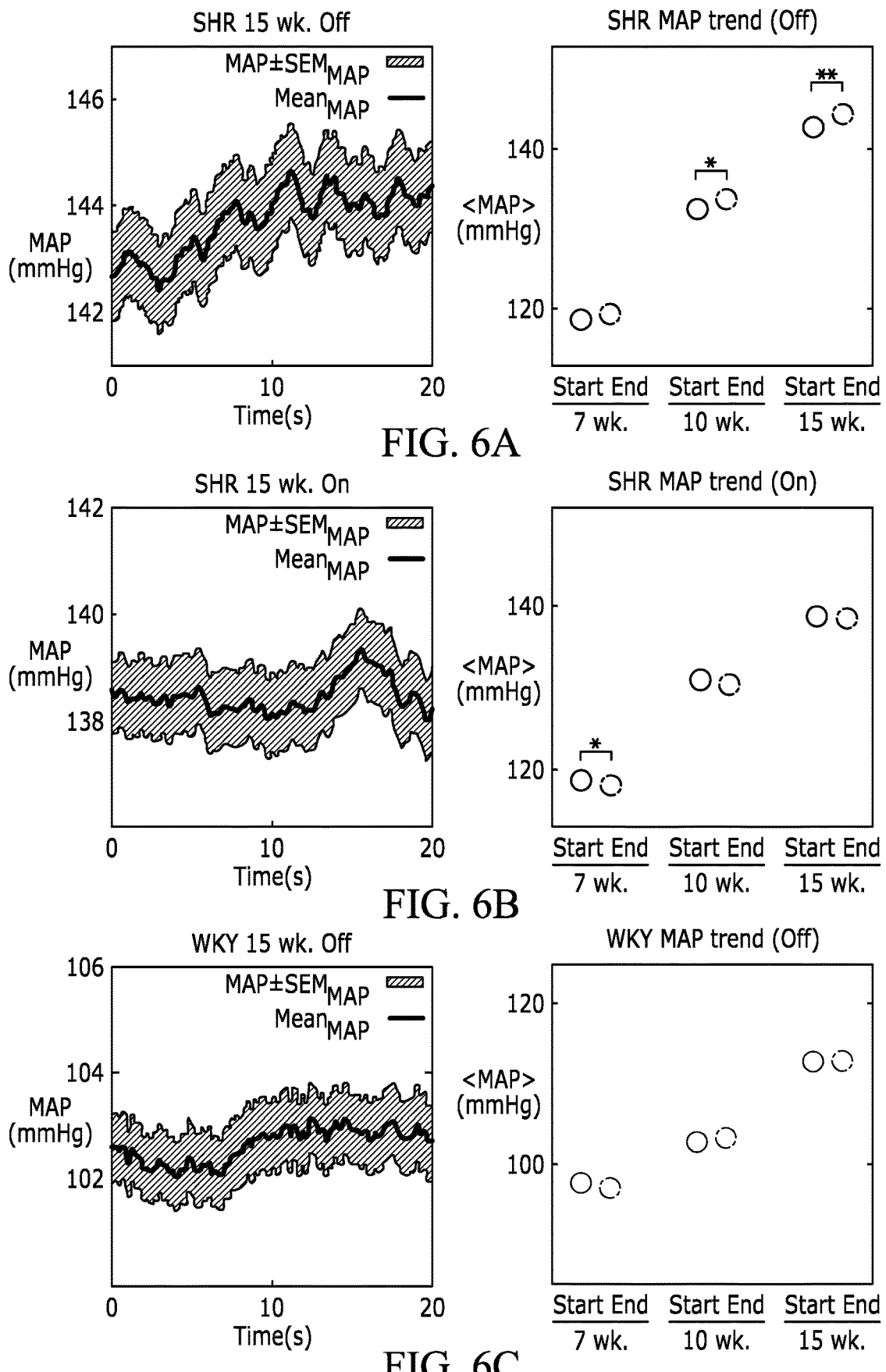
FIG. 6A shows plots of time course mean arterial pressure (MAP) during periods of baroreflex off times for SHR rats at 15 weeks of age.
FIG. 6B shows plots of time course MAP during periods of baroreflex on times for SHR rats at 15 weeks of age.
FIG. 6C shows plots of time course MAP during periods of baroreflex off times for WKY rats at 15 weeks of age.
Figures 6D, 6E, 6F:
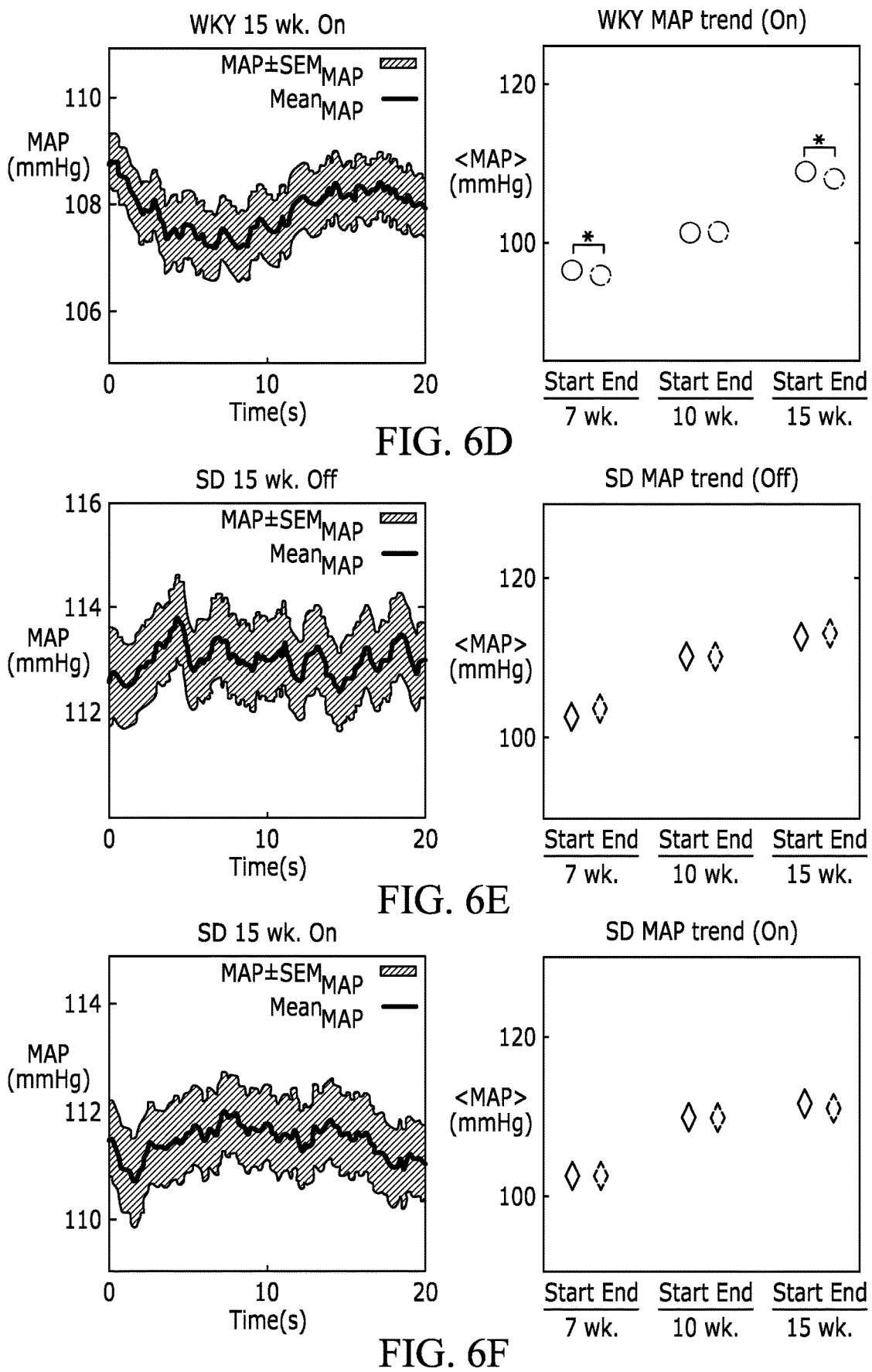
FIG. 6D shows plots of time course MAP during periods of baroreflex on times for WKY rats at 15 weeks of age.
FIG. 6E shows plots of time course MAP during periods of baroreflex off times for SD rats at 15 weeks of age.
FIG. 6F shows plots of time course MAP during periods of baroreflex on times for SD rats at 15 weeks of age.
Figure 6G:
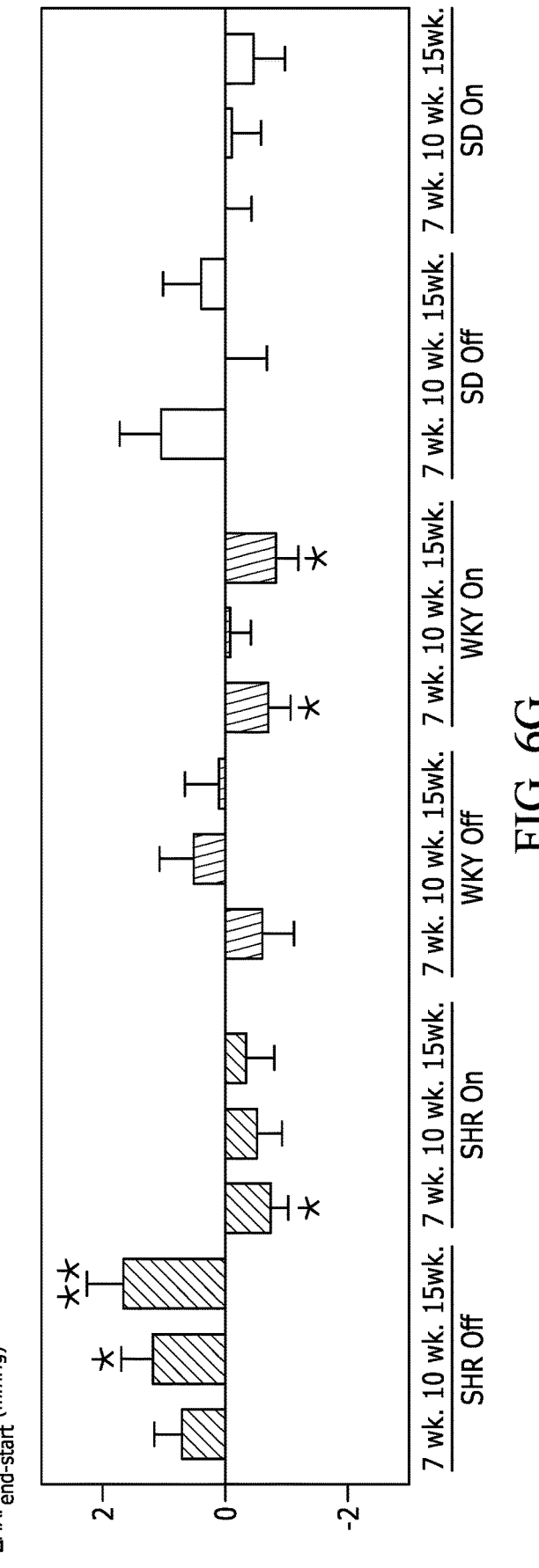
FIG. 6G is a plot that summarizes changes in MAP observed during the initial 20 seconds of baroreflex on and off times

FIGS. 6A-6G shows plots of time courses of MAP during the first 20 seconds of baroreflex on and off times in SHR, WKY, and SD rats at 15 weeks of age. Although there is a high degree of variability in the individual time courses of MAP, the average trend of FIG. 6A (solid black lines in the time-series figures) shows a clear increase with time during off times in the 15-week SHR rats. Similarly, in FIGS. 6B and 6D, there are clear decreases in the average trend during on times in the 15-week SHR and WKY animals. Overall, MAP tended to increase during the off state and tend to decrease when the baroreflex was on state both in the SHR and WKY, with statistically significant increases in MAP during the first 20 seconds of off times are observed for SHR rats at 10 and 15 weeks. Statistically significant decreases in MAP during the first 20 seconds of on times are observed for SHR rats at 7 weeks and WKY rats at 7 and 15 weeks. No significant trends are observed for SD rats at any age. FIG. 6G summarizes the changes in MAP observed during the initial 20 seconds of baroreflex on and off times.

Summarizing the results plotted in FIGS. 5A-5F, and 6A-6G: (i.) both the MAP and the MAP variability were higher during baroreflex "off" state than during the "on" state in only the SHR/WKY model; (ii.) during on and off times 20 s, the MAP tended to increase in the first 20 s during the "off" state and decrease during the "on" state only in the SHR/WKY model; (iii.) in the SHR, the amount that MAP decreases during the first 20 s of "on" states became smaller with age and the onset of the hypertensive phenotype, while the amount that MAP tends to increase in the "off" state increases with age.

Figure 7:
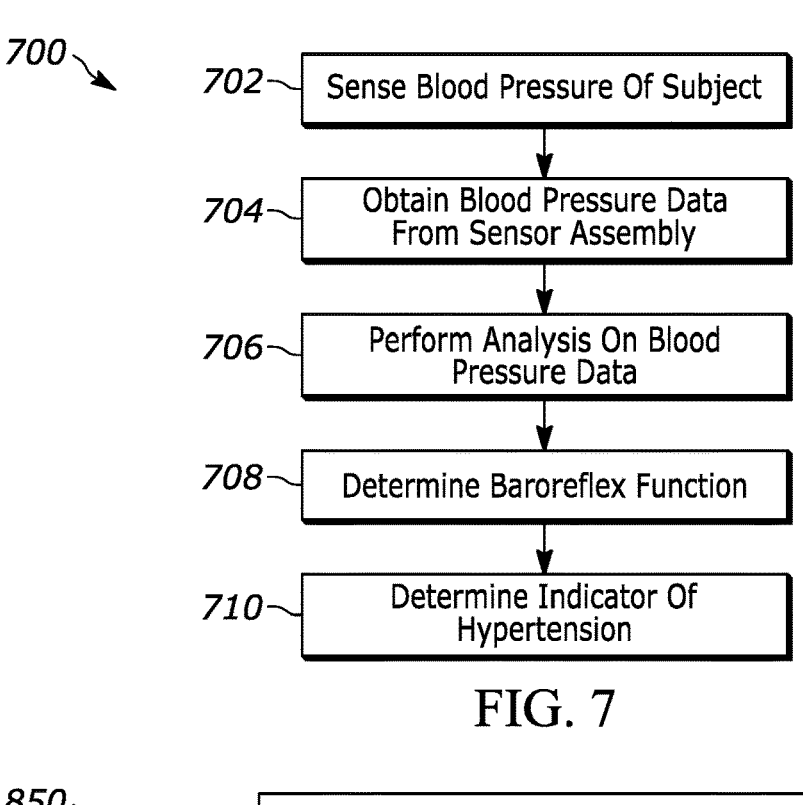
FIG. 7 is a flow diagram of a method for classifying hypertension in a subject.

FIG. 7 is a flow diagram of a method 700 of classifying hypertension in a subject. At block 702, the method 700 includes sensing the blood pressure of a subject. A wearable sensor assembly, according to embodiments described herein, may be used to measure the blood pressure of the subject. The sensor assembly generates a signal indicative of blood pressure data representing the sensed blood pressure. In examples, the blood pressure data may be indicative of a mean arterial pressure waveform. At block 704, the method 700 further includes obtaining the blood pressure data at a processor that is in communication with the wearable sensor array. The processor and wearable sensor assembly may be communicably coupled through any suitable wireless, or wired means. In examples, the processor may be included in the wearable sensor assembly, or the processor may be external and independent from the wearable sensor assembly.

At a block 706, the processor performs a time-series analysis on the blood pressure data and determines the baroreflex function from the blood pressure data at block 708. To determine the baroreflex function, the processor may determine on and off states of the baroreflex functionality, and further determine an on fraction of the baroreflex functionality by comparing the on and off states. At a block 710, the processor determines, from the baroreflex functionality, an indicator of hypertension in the subject. To determine the baroreflex functionality, the processor may compare the blood pressure data to a mathematical model of a baroreflex arc. In examples, the mathematical model may represent a typical hypertensive, or non-hypertensive, baroreflex arc. The processor may compare the determined on fraction to a threshold on fraction amount to determine the indicator of hypertension. Further, to determine the indicator of hypertension, the processor determine a probability density of the blood pressure data, and the processor may compare the probability density of the blood pressure data to probability density data of blood pressure for normal baroreflex functionality. For example, the probability density function may have a mean value that is indicative of a likelihood of developing hypertension. The probability density may have a variance that may be used to determine the indicator of hypertension.

The indicator of hypertension may include one or more of a likelihood of developing hypertension, a prediction of an onset of hypertension, an identification of etiology of hypertension (e.g., the underlying cause of the hypertension being neurogenic, renal, etc.), a prediction to a responsiveness of a treatment (e.g., prediction of a subjects responsiveness to a medication, or other type of treatment), or an identification of a dysfunction associated with autonomic regulation of heart rate such as an abnormally low on fraction (e.g., below 50%, below 40% or below another limit based on age and other factors). The indicator of hypertension may be a binary indication (e.g., an indicator of hypertension or non-hypertension), a probabilistic indication, a probability of hypertension in the future, a score, a classification, or another type of indicator.

In examples, the method 700 may further include sensing, by the wearable sensor assembly, the arterial pulse of the subject and the wearable sensor array may generate a signal indicative of pulse data representing the sensed pulse pressure. In examples, the pulse data may be continuous blood pressure data indicative of a blood pressure of the subject. The continuous blood pressure data may be obtained over night or during a period of time where the subject is asleep. The processor then obtains the pulse data from the wearable sensor assembly, further analyzes the pulse data, and determines the baroreflex functionality from the pulse data. In examples, the obtained pulse data may be data indicative of arterial pressure, systolic pressure, diastolic pressure, heart rate, pulse interval, or another measurable metric indicative of the arterial pulse and/or blood pressure of the subject.

Figure 8:
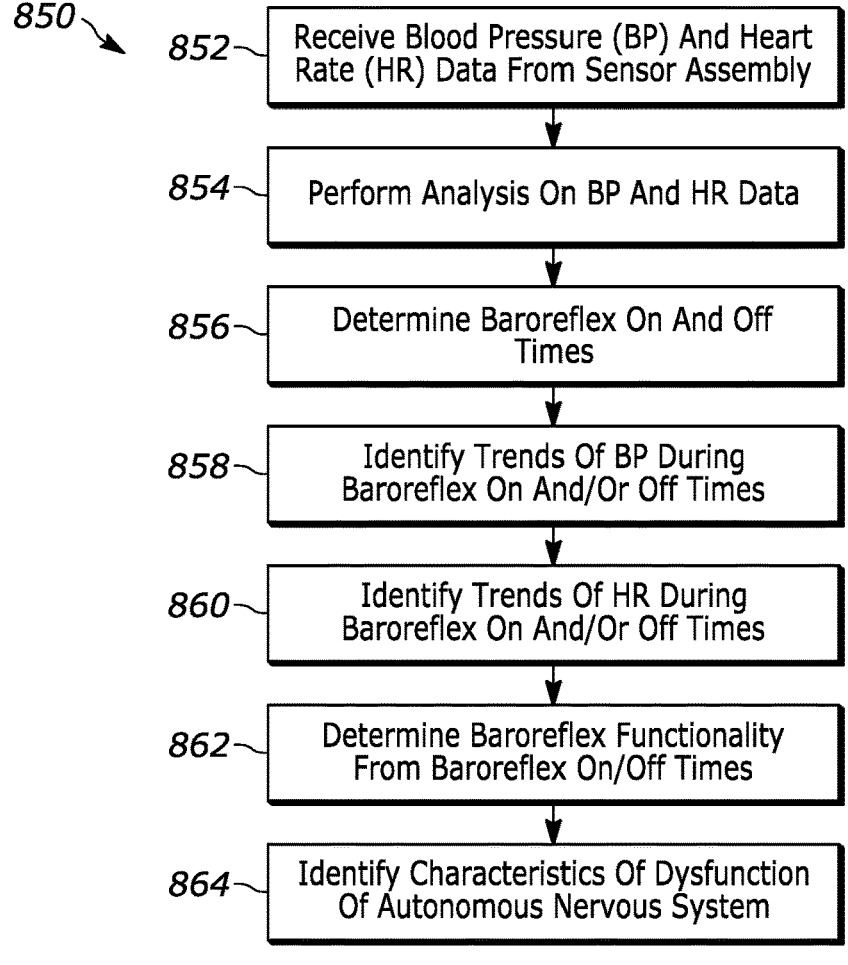
FIG. 8 is a flow diagram of a method for identifying characteristics for diagnosis of dysfunctions of the autonomous nervous system in a subject.

FIG. 8 is a flow diagram of a method 850 for identifying characteristics for diagnosis of dysfunctions of the autonomous nervous system in a subject. The method 850 may be perform by an apparatus as described herein, including a wearable sensor assembly. At a block 852, a signal processor receives blood pressure and heart rate data from the wearable sensor assembly. At a block 854, the signal processor performs statistical analysis on the blood pressure and heart rate data, and determines from the blood pressure and heart rate data, periods of baroreflex on and baroreflex off times at block 856. The baroreflex on times are periods of time when the baroreflex is determined to be controlling the heart rate of the subject, and the baroreflex off times are periods of times when it is determined that the baroreflex is not controlling the heart rate of the subject.

At a block 858, the processor identifies trends of blood pressure during the baroreflex on and/or off times, and at a block 860 the processor identifies trends of heart rate during the baroreflex on and/or off times. The processor then determines baroreflex functionality from the baroreflex on and off times at block 862. To determine the baroreflex functionality, the processor may compare the baroreflex on and off times to determine a baroreflex on fraction. At a block 864, the processor identifies characteristics to use for diagnosis of dysfunctions of the autonomous nervous system of the subject. The characteristics may be identified from one or more of the identified trends of blood pressure, the identified trends of heart rate, and the determined baroreflex function.

The described methods and systems have the ability to identify relatively long time periods, lasting on the order of several minutes, during which the baroreflex system is, and is not, operating in a manner in which fluctuations in arterial pressure are coupled to corresponding fluctuations in heart rate. With the techniques herein, the "on" fraction metric distinguishes between different etiologies of disease in different rat models of hypertension. The "on" fraction metric may therefore be useful in distinguishing between different etiologies of hypertensive disease in humans. Statistical trends in arterial pressure during "on" versus "off" states provide additional classifiers of etiology and are shown to be predictive of the development of hypertension of specific etiologies in animal models. The method and associated algorithms may therefore prove useful in predicting future development of hypertensive disease in humans. Further, the "on" fraction may predict the responsiveness to carotid baroreceptor stimulation (CBS) therapy in patients with resistant hypertension. Thus, the disclosed methods and systems may be used in early diagnosis and prediction of diabetes, severe preeclampsia, acute stroke, heart failure, chronic kidney disease, atherosclerosis, Parkinson's disease, depression, familial dysautonomia, chronic fatigue syndrome (CFS), and the postural orthostatic tachycardia syndrome (POTS).

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. An apparatus comprising:

a wearable sensor assembly attachable to a subject, and comprising a sensor that measures continuous blood pressure data of the subject, the continuous blood pressure data indicative of a blood pressure of the subject;

a signal processor configured to:

receive the continuous blood pressure data from the wearable sensor assembly;

perform time-series analysis on the continuous blood pressure data by extracting, for each cardiac cycle, arterial pressure data and pulse interval data, fitting the arterial pressure data and pulse interval data to a model of a baroreflex arc to generate model-predicted heart rate changes within a fixed time window centered at each cardiac cycle, and comparing the model-predicted heart rate changes to observed heart rate changes to determine, from the continuous blood pressure data, one or more durations of baroreflex on functionality and baroreflex off functionality, wherein the signal processor performs the time-series analysis concurrently with receiving the continuous blood pressure data, wherein the fixed time window is twenty seconds or less and the cardiac cycle being analyzed is positioned at a midpoint of the fixed time window, wherein to determine the one or more durations of baroreflex on functionality, the signal processor is to identify durations of time in the continuous blood pressure data wherein the blood pressure data and the heart rate data are correlated based on the comparison of model-predicted heart rate changes to observed heart rate changes falling within a defined boundary region and wherein to determine the one or more durations of baroreflex off functionality, the signal processor is to identify durations of time in the continuous blood pressure data wherein the blood pressure data and the heart rate data are not correlated based on the comparison falling outside the defined boundary region; determine an indicator of hypertension from the one or more durations of baroreflex on functionality and baroreflex off functionality, wherein the indicator of hypertension is one of a likelihood of developing hypertension, a prediction of an onset of hypertension, an identification of etiology of hypertension, a prediction to a responsiveness of a treatment, or an identification of a dysfunction associated with autonomic regulation of heart rate; and transmit the indicator of hypertension to a treatment system for adjustment of a treatment.

2. The apparatus of claim 1, wherein to determine the indicator of hypertension in the subject from the baroreflex functionality, the signal processor is configured to:

determine a total amount of time of baroreflex on functionality from the one or more durations of baroreflex on functionality; determine a total amount of time of the baroreflex off functionality from the one or more durations of baroreflex off functionality; determine an on fraction of the baroreflex functionality, wherein the on fraction is a ratio of the total amount of time of baroreflex on functionality and the total amount of time of the baroreflex off functionality; and compare the on fraction of baroreflex on functionality to a range of values of baroreflex on functionality, wherein the indication of hypertension is determined from whether the on fraction of baroreflex functionality is within the range of values or outside of the range of values.

3. The apparatus of claim 1, wherein to determine the indicator of hypertension in the subject from the one or more durations of baroreflex on functionality and baroreflex off functionality, the signal processor is configured to: identify one or more trends in the continuous blood pressure data during the durations of the baroreflex on functionality; and determine the indicator of hypertension from the one or more identified trends.

4. The apparatus of claim 1, wherein to determine the indicator of hypertension in the subject from the one or more durations of baroreflex on functionality and baroreflex off functionality, the signal processor is configured to: identify one or more trends in the continuous blood pressure data during the durations of the baroreflex off functionality; and determine the indicator of hypertension from the one or more identified trends.

5. The apparatus of claim 1, wherein to determine the indicator of hypertension in the subject from the one or more durations of baroreflex functionality, the signal processor is configured to:

determine a first probability density of the continuous blood pressure data during the one or more durations of baroreflex on functionality, the first probability density having a mean of the data in the durations of baroreflex on functionality, a variance of the data in the durations of baroreflex on functionality, and a probability density profile; determine a second probability density of the continuous blood pressure data during the one or more durations of baroreflex off functionality, the second probability density having a mean of the data in the durations of baroreflex off functionality, and a variance of the data in the durations of baroreflex off functionality, and a probability density profile; and determine the indicator of hypertension by comparing the first probability density and the second probability density.

6. The apparatus of claim 5, wherein comparing the first probability density and the second probability density comprises one of comparing the mean of the first probability density and the mean of the second probability density, comparing the variance of the first probability density and the variance of the second probability density, comparing the probability density profile of the first probability density and the probability density profile of the second probability density.

7. The apparatus of claim 5, wherein determining the indicator of hypertension further comprises determining the indicator of hypertension by comparing one of the first probability density profile or second probability density profile with a probability density profile of normal baroreflex functionality.

8. The apparatus of claim 1, wherein the blood pressure data comprises mean arterial pressure waveform data.

9. The apparatus of claim 1, wherein the wearable sensor assembly comprises at least one of an optical heart rate sensor, a physical pressure sensor, a transducer, an invasive catheter, an electrocardiography sensor, a photoplethysmography sensor, a sphygmomanometer, an inflatable cuff, or a digital blood pressure monitor.

10. A method for classification of hypertension comprising:

sensing, by a wearable sensor assembly having a sensor, continuous blood pressure data of a subject, wherein the continuous blood pressure data is indicative of a blood pressure of the subject, wherein the continuous blood pressure data comprises arterial pressure data and heart rate data of the subject; obtaining, by a processor in communication with the wearable sensor assembly, the continuous blood pressure data; performing, by the processor, time-series analysis on the continuous blood pressure data by extracting, for each cardiac cycle, arterial pressure data and pulse interval data, fitting the arterial pressure data and pulse interval data to a model of a baroreflex arc to generate model-predicted heart rate changes within a fixed time window centered at each cardiac cycle, and comparing the model-predicted heart rate changes to observed heart rate changes to determine, by the processor and from the continuous blood pressure data, one or more durations of baroreflex on functionality and baroreflex off functionality, wherein the processor performs the time-series analysis concurrently with receiving the continuous blood pressure data, wherein the fixed time window is twenty seconds or less and the cardiac cycle being analyzed is positioned at a midpoint of the fixed time window, wherein determining the one or more durations of baroreflex on functionality comprises identifying durations of time in the continuous blood pressure data wherein the blood pressure data and the heart rate data are correlated based on the comparison of model-predicted heart rate changes to observed heart rate changes falling within a defined boundary region and wherein determining the one or more durations of baroreflex off functionality comprises identifying durations of time in the continuous blood pressure data wherein the blood pressure data and the heart rate data are not correlated based on the comparison falling outside the defined boundary region;

determining, by the processor, an indicator of hypertension from the one or more durations of baroreflex on functionality and baroreflex off functionality, wherein the indicator of hypertension is one of a likelihood of developing hypertension, a prediction of an onset of hypertension, an identification of etiology of hypertension, a prediction to a responsiveness of a treatment, or an identification of a dysfunction associated with autonomic regulation of heart rate; and transmitting the indicator of hypertension to a treatment system for adjustment of a treatment.

11. The method of claim 10, wherein determining the indicator of hypertension in the subject from the baroreflex functionality comprises:

determining, by the processor, a total amount of time of baroreflex on functionality from the one or more durations of baroreflex on functionality;

determining, by the processor, a total amount of time of the baroreflex off functionality from the one or more durations of baroreflex off functionality; determining, by the processor, an on fraction of the baroreflex functionality, wherein the on fraction is a ratio of the total amount of time of baroreflex on functionality and the total amount of time of the baroreflex off functionality; and comparing, by the processor, the on fraction of baroreflex on functionality to a range of values of baroreflex on functionality, wherein the indication of hypertension is determined from whether the on fraction of baroreflex functionality is within the range of values or outside of the range of values.

12. The method of claim 10, wherein to determining the indicator of hypertension in the subject from the one or more durations of baroreflex on functionality and baroreflex off functionality comprises: identifying, by the processor, one or more trends in the continuous blood pressure data during the durations of the baroreflex on functionality; and determining, by the processor, the indicator of hypertension from the one or more identified trends.

13. The method of claim 10, wherein determining the indicator of hypertension in the subject from the one or more durations of baroreflex on functionality and baroreflex off functionality comprises: identifying, by the processor, one or more trends in the continuous blood pressure data during the durations of the baroreflex off functionality; and determining, by the processor, the indicator of hypertension from the one or more identified trends.

14. The method of claim 10, wherein determining the indicator of hypertension in the subject from the one or more durations of baroreflex functionality comprises:

determining, by the processor, a first probability density of the continuous blood pressure data during the one or more durations of baroreflex on functionality, the first probability density having a mean of the data in the durations of baroreflex on functionality, a variance of the data in the durations of baroreflex on functionality, and a probability density profile; determining, by the processor, a second probability density of the continuous blood pressure data during the one or more durations of baroreflex off functionality, the second probability density having a mean of the data in the durations of baroreflex off functionality, and a variance of the data in the durations of baroreflex off functionality, and a probability density profile; and determining, by the processor, the indicator of hypertension by comparing the first probability density and the second probability density.

15. The method of claim 10, wherein the blood pressure data comprises mean arterial pressure waveform data.

16. The method of claim 10, wherein the wearable sensor assembly comprises at least one of an optical heart rate sensor, a physical pressure sensor, a transducer, an invasive catheter, an electrocardiography sensor, a photoplethysmography sensor, a sphygmomanometer, an inflatable cuff, or a digital blood pressure monitor.

17. An apparatus comprising:

a wearable sensor assembly attachable to a subject, and comprising a sensor that measures continuous blood pressure data of the subject, the continuous blood pressure data indicative of a blood pressure of the subject;

a signal processor configured to:

receive the continuous blood pressure data from the wearable sensor assembly;

perform time-series analysis on the continuous blood pressure by extracting, for each cardiac cycle, arterial pressure data and pulse interval data, fitting the arterial pressure data and pulse interval data to a model of a baroreflex arc to generate model-predicted heart rate changes within a fixed time window centered at each cardiac cycle, and comparing the model-predicted heart rate changes to observed heart rate changes to determine, from the continuous blood pressure data, one or more durations of baroreflex on functionality and baroreflex off functionality, wherein the signal processor performs the time-series analysis concurrently with receiving the continuous blood pressure data, wherein the fixed time window is twenty seconds or less and the cardiac cycle being analyzed is positioned at a midpoint of the fixed time window;

analyze the one or more durations of baroreflex on functionality and baroreflex off functionality to determine an indicator of hypertension, wherein the indicator of hypertension is one of a likelihood of developing hypertension, a prediction of an onset of hypertension, an identification of etiology of hypertension, a prediction to a responsiveness of a treatment, or an identification of a dysfunction associated with autonomic regulation of heart rate; and transmit the indicator of hypertension to a treatment system for adjustment of a treatment.

\* \* \* \* \*